US005468727A

United States Patent [19]
Phillips et al.

[11] Patent Number: 5,468,727
[45] Date of Patent: * Nov. 21, 1995

[54] METHODS OF NORMALIZING METABOLIC PARAMETERS IN DIABETICS

[75] Inventors: William T. Phillips; Joyce G. Schwartz; Gary M. Green, all of San Antonio, Tex.

[73] Assignee: Board of Regents, The University of Texas System

[*] Notice: The portion of the term of this patent subsequent to Feb. 16, 2010, has been disclaimed.

[21] Appl. No.: 19,159

[22] Filed: Feb. 16, 1993

Related U.S. Application Data

[63] Continuation-in-part of Ser. No. 626,579, Dec. 13, 1990, Pat. No. 5,187,154.
[51] Int. Cl.$^6$ .......................... C07K 14/00; A61K 38/16
[52] U.S. Cl. .................. 514/12; 514/13; 514/14; 514/15; 514/16; 530/324
[58] Field of Search ................... 514/12, 13, 14, 514/15, 16; 530/324

[56] References Cited

PUBLICATIONS

Koizuma et al., Biomed. Res. (1989) 10 (Suppl. 1) pp. 45–50. Abstract.
Hill et al., Physiol. Behav. (1990 Aug). 48(2) pp. 241–246.
Barnett et al., Gastroenterology 94(3) 739–44 (1988).
Granneman et al., Am. J. Physiol. 247 (6 pt. 2) R1054–R1061 (1984).

Primary Examiner—Jill Warden
Assistant Examiner—Carol A. Salata
Attorney, Agent, or Firm—Arnold, White & Durkee

[57] ABSTRACT

The invention relates to a method of diagnosing and treating individuals with diabetes or at risk to develop diabetes mellitus. In particular, gastric emptying determinations are used to assess risk. Risk or early symptoms associated with subsequent development of diabetes mellitus may be controlled or alleviated by delaying gastric emptying. Delay or inhibition of gastric emptying is sufficient to restore gastric emptying within normal ranges as determined by restoration of typical glucose metabolic parameters such as blood glucose and insulin levels to normal or near normal ranges. The method is also useful in prophylactic treatment of individuals at high risk to develop diabetes mellitus, such as the obese, those with a family history of diabetes and those of particular ethnic and minority groups.

10 Claims, 25 Drawing Sheets

METHODS OF NORMALIZING METABOLIC PARAMETERS IN DIABETICS

The Government may have certain rights in the invention pursuant to grant No. 2-S07-RR07187-11. This is a continuation-in-part of application Ser. No. which is now U.S. Pat. No. 5,187,154 issued Feb. 16, 1993.

BACKGROUND OF THE INVENTION

1. Field of the Invention

The invention relates to a method of identifying and treating patients having early, recently diagnosed noninsulin-dependent diabetes and to compositions useful in the treatment of such diabetics. In particular, the method involves the use of compositions that effectively raise plasma cholecystokinin levels thereby alleviating rapid gastric emptying and restoring various glucose metabolic indicators to normal or near-normal levels.

2. Description of Related Art

In recent years the role of the stomach in glucose homeostasis has become recognized. In 1982, Thompson, et al. described gastric emptying as an important determinant of the oral glucose tolerance test and suggested that the glucose tolerance test could be used to assess gastric emptying. In 1983 Brener et al. described characteristic gastric emptying of glucose solutions in normal human subjects. Those studies showed that glucose empties from the stomach in a constant and linear fashion at an average of 2.13 kcal/min regardless of the concentration of the glucose solution. Prior to this study, it was widely believed that all liquids emptied in an exponential manner. It is Brener's hypothesis that a dynamic "closed loop" feedback interrelationship exists between the stomach and the duodenum to control the delivery of calories from the stomach.

Keshavarzian et al. (1987) have studied gastric emptying in a heterogeneous group of diabetics with insulin-dependent diabetes mellitus and non-insulin dependent diabetes mellitus who had been diagnosed with the disease for more than 5 years. Although Keshavarzian emphasized the delay in gastric emptying, particularly with solids, some diabetic subjects in the study exhibited a more rapid gastric emptying compared to controls. Liquid gastric emptying was generally the same for both the controls and diabetics with the gastric half-emptying time (t½) showing no significant difference. It was noted that some of the patients exhibited abnormally fast emptying of liquids, but Keshavarzian, et al. attached no significance to the observation.

Campbell et al. (1977) described delayed gastric emptying in 10 of 12 diabetic subjects. Although the majority of the patients showed delayed gastric emptying, two of the subjects exhibited more rapid gastric emptying rates compared with controls.

Horowitz et al. (1989) described delayed gastric and esophageal emptying in 20 subjects with non-insulin dependent diabetes mellitus. The duration of known diabetes in the subjects ranged from 1–20 years. Although two of the subjects exhibited more rapid than normal liquid gastric emptying, the group of 20 as a whole exhibited delayed liquid gastric emptying (t½) slower than in normal patients, $p<0.05$. There was significant delay of solid food emptying in these patients (increased retention of solid food at 100 min, $p<0.001$).

Gastric emptying has been studied as a non-invasive diagnostic tool as an indicator of metabolic and neural disturbances. For example, chronic forms of gastric stasis can be caused by innervation abnormalities in diabetics with autonomic neuropathy (Smout, 1986). Many other conditions have been studied, including those in patients who had stomach operations or diseases of the gastrointestinal tract. Generally, the majority had delayed gastric emptying (Pellegrini, et al., 1983). In particular, delayed gastric-emptying appears to be a phenomenon associated with diabetes.

Methods of regulating pyloric functions are known in the art. Diabetic gastroparesis and hypertrophic pyloric stenosis are examples of conditions successfully treated (Akkermans, et al., 1989); delayed gastric emptying has been treated with drugs that accelerate the emptying process; for example, metoclopramide or domperidone. An opposite effect is shown by Propantheline and opiates which delay gastric emptying (Chaudhuri, et al., 1990).

There is some information on the effects of different compounds on enzyme components of pancreatic secretion, for example, the role of cholecystokinin (CCK) (Liddle, et al., 1988) and possible regulatory control by other gut hormones, such as VIP which stimulate insulin release from the pancreas (Schwartz, et al., 1990). It is known that CCK has a significant role in regulating glucose homeostasis in humans (Liddle, et al., 1988) and that it delays gastric emptying and reduces hyperglycemia (Jenkins, et al., 1990). However, the connection between CCK secretion on gastric emptying and insulin release in normal and diabetic patients has not yet been fully evaluated (Liddle, 1990).

Studies so far reported indicate that in diabetic patients, delayed gastric emptying is typical. However, until now, there was no realization that certain classes of patients, those not yet manifesting overt diabetes, those at risk to develop diabetes, those in early stages of diabetes and many patients having non-insulin dependent diabetes, exhibit abnormally rapid gastric emptying. It was this unexpected and surprising discovery that led to the development of a method of a simple treatment. By delaying gastric emptying in this group of patients at high risk to develop diabetes, or in those with recent onset of diabetes, insulin and plasma glucose levels after a meal may be maintained at levels much closer to normal nondiabetic levels. This allows a delay of nutrient absorption which has been recognized to result in increased economy of glucose disposal and insulin economy (Jenkins, et al., 1990). This is a first and significant step in early treatment of those at risk for developing debilitating forms of diabetes, even insulin-dependent diabetes, and may delay or forestall completely the usual progress of the disease.

SUMMARY OF THE INVENTION

The invention is based on the unexpected and surprising discovery that early non-insulin dependent diabetics exhibit significantly more rapid gastric emptying than normal controls. This finding forms the rationale for methods of diagnosis and for treatments designed to delay the onset of symptomatic diabetes and possibly to alter the course of the disease. Treatment is based on the use of compounds that delay gastric emptying, which then leads to normalization of blood glucose and other metabolic parameters.

In general, the invention relates to a method of restoring or maintaining glucose metabolic indicators at normal or near-normal levels in a diabetic or prediabetic animal or human exhibiting rapid gastric emptying. The method utilizes a substance that will alter gastric emptying and is given in an amount to delay gastric emptying so that normal or near normal emptying rates are attained.

Glucose metabolic indicators relate to interconnected metabolic events. Such parameters include blood glucose levels, blood insulin levels, post prandial glucose and insulin levels, hemoglobin A1C, C-peptide, quantitation of insulin resistance and blood levels of gastric inhibitory peptide (GIP) and cholecystokinin (CCK). One or more of these parameters may exceed normal range without indication to the individual that altered metabolic patterns are developing. These patterns are frequently very early symptoms of diabetes mellitus. For example, blood glucose levels may be high and sugar may be present in the urine. An individual may experience increased thirst and frequency in urination or, in females, vaginal yeast infections without awareness that a health problem exists or is developing. Some of these subjects may exhibit rapid gastric emptying. Regulation of gastric emptying is complex, but delaying gastric emptying appears to slow delivery of glucose to the duodenum thereby reducing postprandial hyperglycemia. Therefore, in delaying gastric emptying, a treatment is provided which may control the development or at least delay the onset of symptoms that are frequently associated with the onset of diabetes mellitus.

Diabetes mellitus in its early stages may exhibit symptoms that are virtually unnoticed. As the disease develops, later stages may include problems with vision, neuropathy and a marked increase in the number of infections. Later stages of the disease may be associated with loss of vision and atherosclerosis, the latter resulting in circulatory problems, including coronary heart disease and amputations.

A particular aspect of the invention therefore is the treatment of a mammal, particularly a human, exhibiting rapid gastric emptying and also showing signs of an early or prediabetic condition, such as elevated blood glucose levels, glycosuria or high levels of endogenous insulin. Using this method of treatment, one first identifies an early or prediabetic condition in an individual. In the more usual circumstance, gastric emptying studies are performed after these symptoms appear; however, some groups of individuals are known to be at risk to develop diabetes. These groups include the morbidly obese, those with a family history of diabetes and most particularly certain ethnic or minority groups, including Hispanics, Eskimos, American Indians, Asian Indians, Chinese, Japanese, Polynesians and those of Jewish descent. In such cases, prudent medical practice would indicate a test of gastric emptying rates. Individuals exhibiting abnormally rapid gastric emptying would then be treated with a therapeutically effective dose of a gastric emptying inhibiting substance, e.g., POT II, a noncaloric substance. This will be an amount sufficient to alleviate or eliminate symptoms/signs associated with early or prediabetes, particular symptoms/signs including elevated blood glucose and insulin levels, insulin resistance, increased susceptibility to infection and/or glycosuria while also maintaining gastric emptying within normal levels. Individuals at risk or in early stages of diabetes may generally be identified by measuring blood glucose and insulin peak levels after glucose administration.

Any of a number of known gastric emptying inhibiting substances may be used to delay gastric emptying, including gut hormones (e.g., cholecystokinin) and analogs, aluminum hydroxide compounds, opiates, estrogens, trypsin inhibitors and tricyclic compounds. Some useful polypeptides might include bombesin, somatostatin, secretin, gastric inhibitory peptide (GIP), VIP, glucagon or gastrin. Propantheline is recognized as delaying gastric emptying. Trypsin inhibitors are expected to be useful, including Proteinase Inhibitor II, Bowman-Birk inhibitor and Camostat. Preferred compounds are Proteinase Inhibitor II (POT II) and cholecystokinin. Cholecystokinin has been well studied in humans and is known to effectively delay gastric emptying (Liddle, 1986). Other compounds delaying gastric emptying may be used, including substances that act directly to stimulate a feedback which effectively delays gastric emptying. Certain noncaloric substances will also be useful, such as POT II and Bowman-Birk inhibitor. As used herein, noncaloric is intended to mean substances that provide virtually no calories compared with counterpart foodstuffs, for example, the noncaloric sweeteners such as aspartame or saccharin which would be compared with peptides or sugars that are digested and provide calories.

The invention is also envisioned as useful in assessing risk of diabetes mellitus in subjects who do not show any abnormalities in glucose metabolism but who have other factors which experience has shown indicate a tendency to develop diabetes mellitus. For example, the morbidly obese, those with a family history of diabetes, those with mature onset diabetes. Non-insulin dependent diabetes is typically seen in individuals over 30 years of age who initially are able to control the diabetes through diet or oral hypoglycemic drugs.

Another risk group is women who develop diabetes during pregnancy, often distinguished as gestational diabetes because it may first appear to develop during pregnancy. Women with gestational diabetes mellitus have an increased likelihood of remaining carbohydrate intolerant after pregnancy, a significantly increased risk of noninsulin dependent diabetes later in life and a predisposition to obesity, hyperlipidemia, atherosclerotic vascular disease and mortality. Babies from these pregnancies have an increased risk of birth defects, a higher incidence of childhood obesity and type II diabetes during childhood. Rapid gastric emptying in the mother would indicate a potential to develop high blood sugar. Control through delaying of gastric emptying might prevent detrimental effects on the fetus during the pregnancy.

Gastric emptying rates may be measured using dye dilution methods and x-ray images after a barium-loaded meal. More preferable techniques include sonography, electrical impedance or scintigraphic methods which are rapid and noninvasive. A most preferable method is scintigraphic determination of ingested $^{99m}$technetium-sulfur colloid using a low energy gamma camera.

Yet another aspect of the invention is a pharmaceutical composition which combines insulin and cholecystokinin in a vehicle suitable for injection or ingestion. This may be saline, a suitable buffer such as phosphate or acetate, an oil-based vehicle or the like. pH modifying substances may be added if necessary to maintain near-neutral or slightly acidic pH. A most preferable mode of injection is intramuscular or subcutaneous because this is normally the mode by which most diabetics self-administer insulin. This composition would be suitable for patients who require insulin and exhibit rapid gastric emptying.

The invention also comprises a pharmaceutical composition of a compound that delays gastric emptying and an oral hypoglycemic in an orally acceptable pharmaceutical formulation. Pharmaceutically acceptable formulating agents include powders, granules, capsules, coated tablets, syrupy preparations and aqueous suspensions. Formulating agents employed may be solid or liquid, including but not limited to such solids as calcium phosphate, calcium carbonate, dextrose, sucrose, dextrin, sucrose ester, starch, sorbitol, mannitol, crystalline cellulose, talc, kaolin, synthetic aluminum silicate, carboxymethyl cellulose, methylcellulose, cellulose acetate phthalate, alginates, polyvinyl pyrrolidone, polyvinyl alcohol, gum arabic, tragacanth gum, gelatin, bentonite, agar powder, shellac, Tween 80, carrageenans and psyllium. Flavor enhancers may be added to oral preparations, including taste masking substances such as sweeteners and citrus flavors. Other additives, including color, preservatives, bulk or antifoam agents may also be included in the formulation. Examples of compounds that delay gastric emptying and may be administered orally are trypsin/chymotrypsin inhibitors, preferably Pot II or Camostat. These may be mixed with any suitable oral hypoglycemic indicated for the patient, such as chlorpropamide, tolbutamide, tolazamide, glipizide or glyburide.

DESCRIPTION OF THE PREFERRED EMBODIMENTS

EXAMPLE 1

Figure 1:
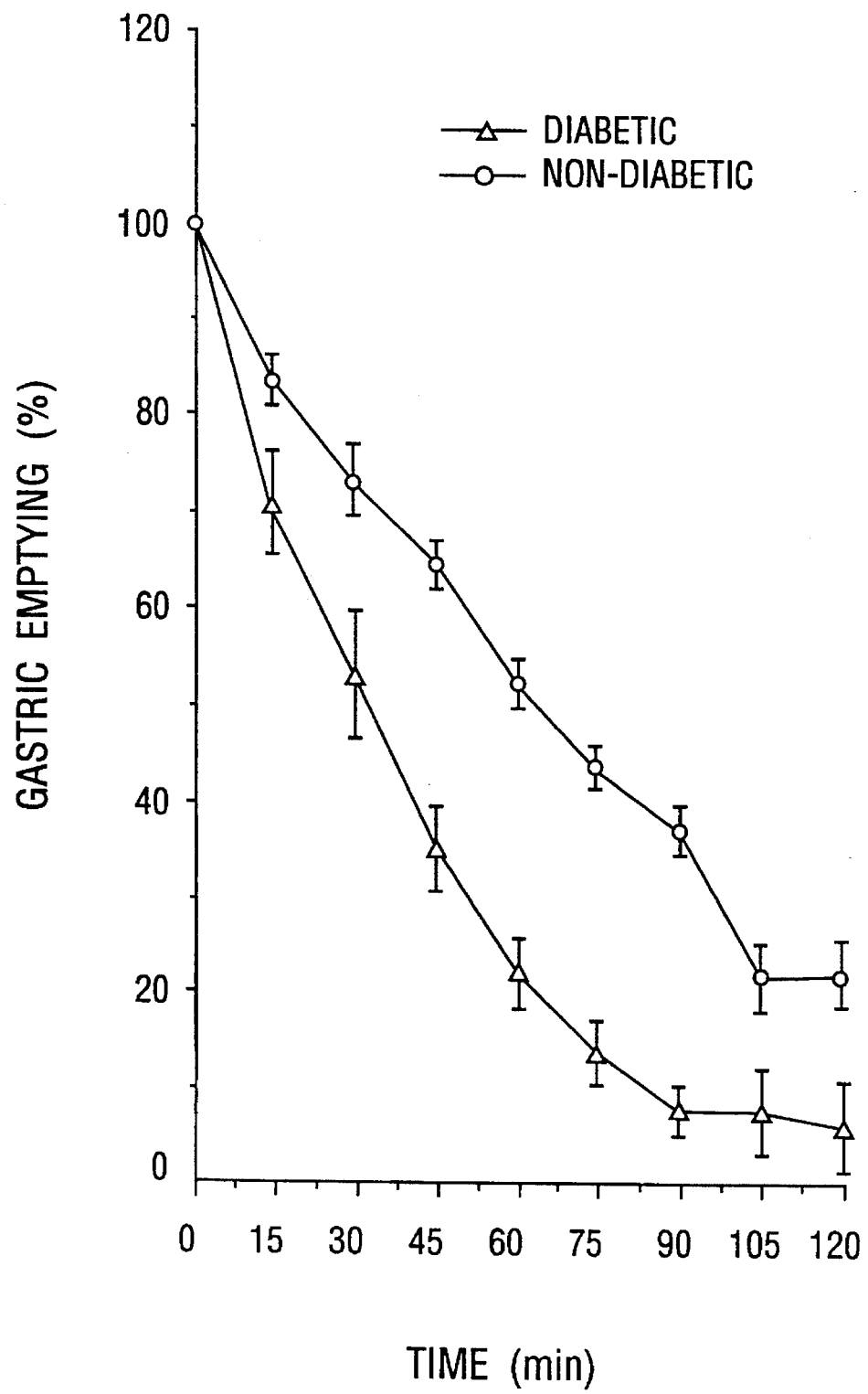
FIG. 1 shows the gastric emptying pattern of six subjects with non-insulin dependent diabetes mellitus and an equal number of age and sex-matched controls.

The discovery that early stage Type II diabetics exhibit rapid gastric emptying was unexpected. Typically, delayed gastric emptying is observed in most cases associated with diabetes. The results suggested that control of rapid gastric emptying might delay the onset of more serious complications of diabetes and/or normalize indicators of glucose metabolism such as blood sugar levels.

Subjects

Six subjects with early NIDDM (diagnosed for less than two years) and six sex- and age-matched nondiabetic subjects underwent gastric emptying studies. The subjects (10 males, 2 females) ranged in age from 35 to 62 years of age. Five of the six subjects with NIDDM were Hispanic Americans, one an Iranian. All 6 non-diabetic subjects were non-Hispanic Caucasians with normal fasting glucose values. The subjects with NIDDM had been previously diagnosed as being diabetic using a 75 g oral glucose tolerance test (OGTT) with blood sampled fasting and at 2 hr according to current WHO criteria. All the subjects with NIDDM were taking oral hypoglycemic medication which they discontinued the evening prior to the study. All studies were begun between 7–8 am following a 12 hr fast.

Statistical Methods

The data were analyzed using a paired t-test. The gastric half-emptying time for each patient was calculated by linear interpolation.

Gastric Emptying in Human Subjects

Gastric emptying studies utilizing a gamma camera (Scintronix USA Inc., Woburn Mass., USA) were performed with a modified 0.62M (50 g glucose in 450 ml water) glucose solution. The use of this glucose solution in gastric emptying has been previously studied (Schwartz, et al., 1990). Approximately 200 µCi of 99 metastable technetium sulfur colloid ($^{99m}$Tc-SC, CIS-US, Bedford, Mass., USA) were added and mixed with the glucose solution. The subjects drank the glucose solution in its entirety in a 5 minute span shortly after the $^{99m}$Tc-SC had been added to the solution.

The subjects were then placed in a semi-reclining position (45 degrees from horizontal) and the gamma camera was positioned anteriorly. Only anterior views were used in calculating the gastric emptying since it has been shown (Christian, et al., 1983) that the geometric means of the anterior and posterior projections, using liquid meals, were very similar to those of the anterior views alone. Data were collected continuously and summed at 60 second intervals. Images were acquired during an interval of 120 minutes. Blood samples were drawn at 15 minute intervals beginning just prior to ingestion of the glucose solution and ending at 120 minutes. The blood was collected in vacutainer tubes containing potassium oxalate and sodium fluoride (Becton Dickinson Vacutainer Systems, Rutherford, N.J.,USA). Glucose analysis was performed on a Paramax instrument (Baxter Healthcare Corp., Irvine, Calif., USA).

The Scintronix gamma camera was used with low energy, all purpose collimator at a 20% window setting centered at 140 keV. The camera was connected to a Medical Data Systems Computer (Ann Arbor, Mich., USA). Counts in the stomach region of interest were calculated in each 60 second image. After correcting for radioactive decay, the count rates were converted to percentage of the maximum count rate recorded.

Figure 2:
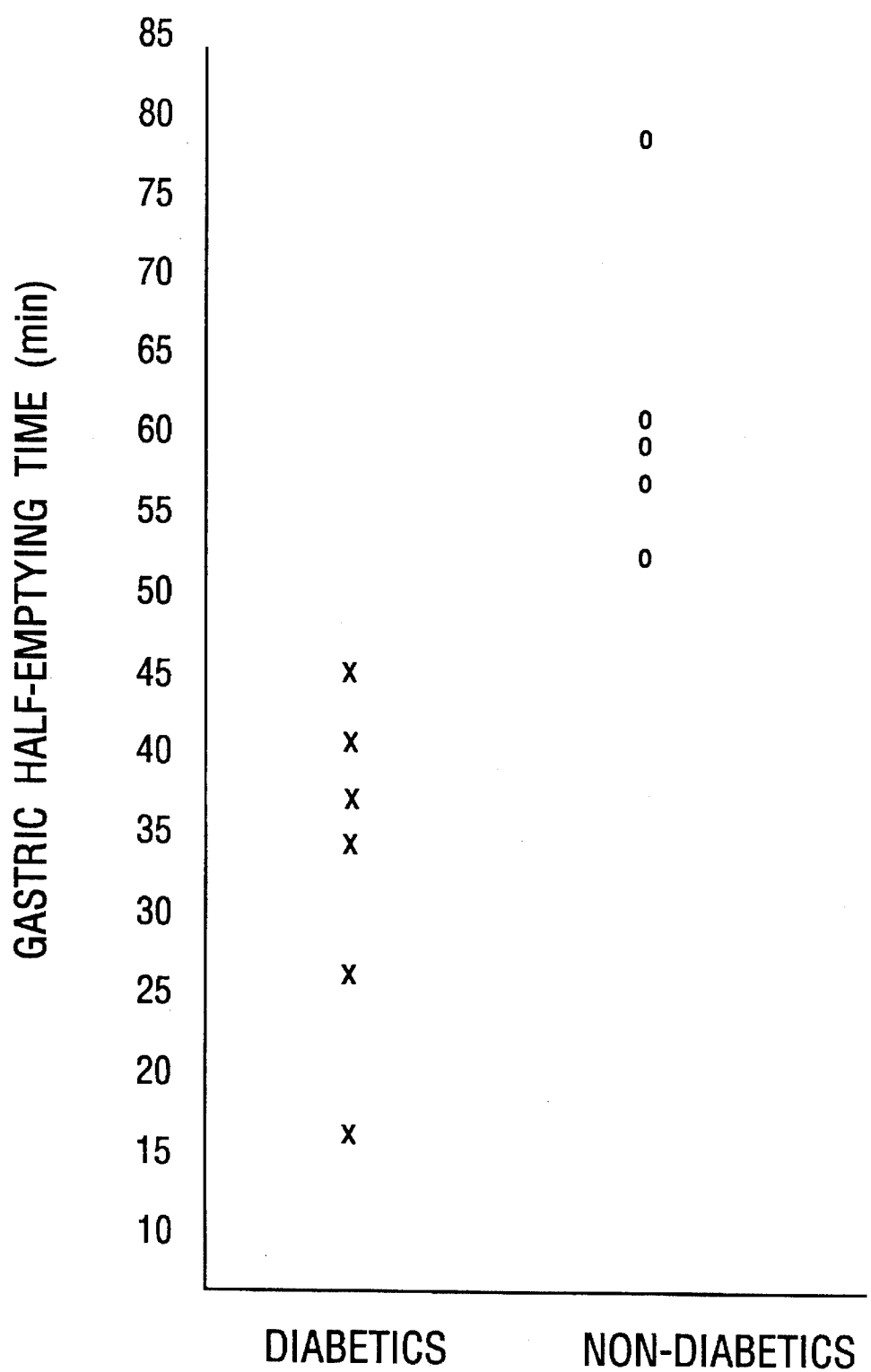
FIG. 2 compares the half-emptying time for subjects with non-insulin dependent diabetes and non-diabetics.
Figure 3:
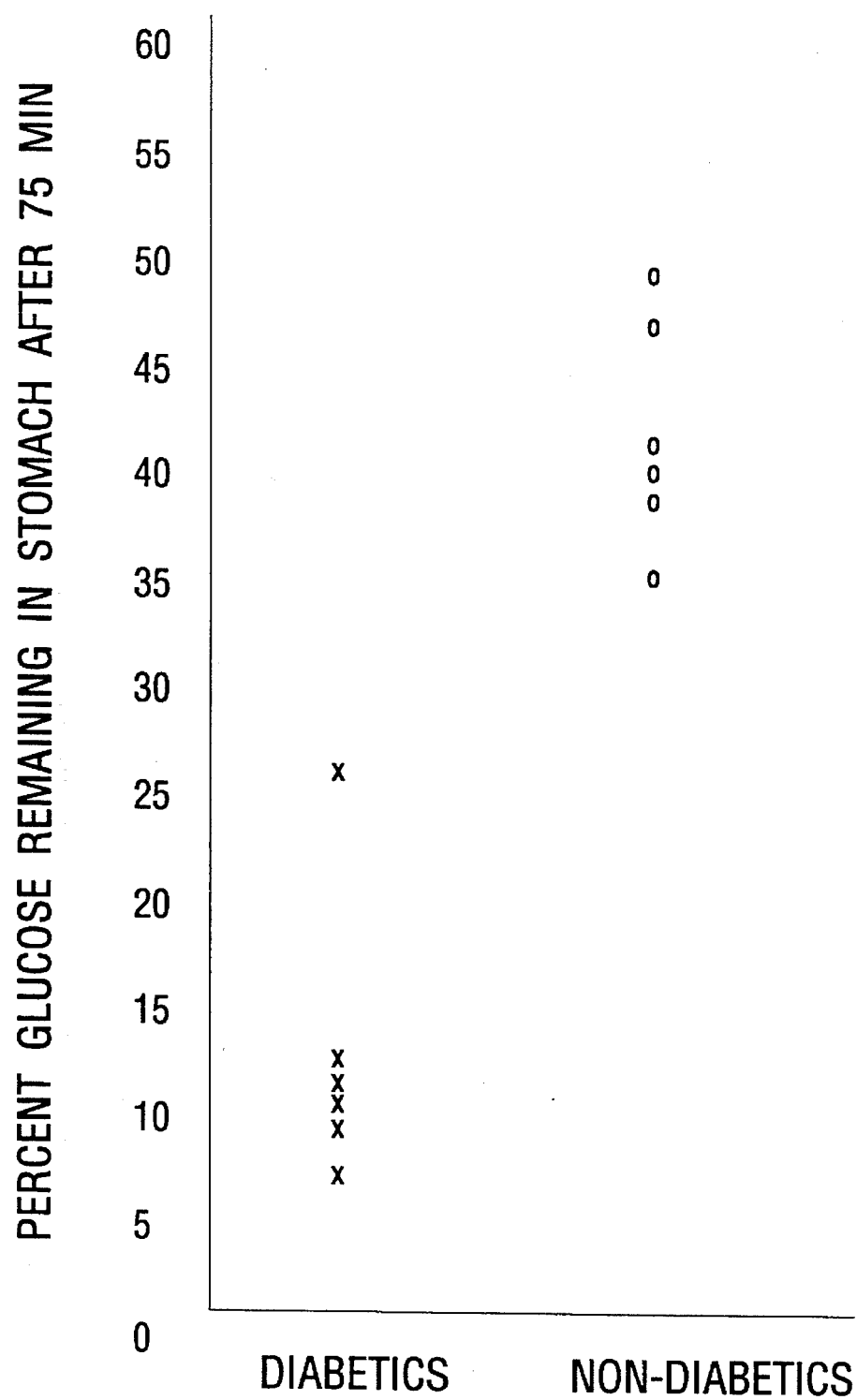
FIG. 3 shows the percent glucose remaining in the stomach 75 min after administration to non-insulin dependent diabetes mellitus patients and to control patients.

The half emptying time was significantly ($P=0.009$) shorter for the subjects with non-insulin dependent diabetes (average=32.6 min, SE=5.5) than for the non-diabetics (average=64.3, SE=5.5) as shown in FIGS. 1 and 2. The area under the gastric-emptying curve during the first hour, representing an overall time-weighted average, for the subjects with non-insulin dependent diabetes mellitus was 74% of the area under the curve for the non-diabetics ($P=0.016$). The area under the curve during the two hours for the subjects with NIDDM was 60% of the area under the curve for the non-diabetics ($P=0.002$). The half-emptying time and the area under the curve indicate substantially faster emptying for the subjects with NIDDM. The largest mean separation between subjects with NIDDM and non-diabetics occurred at 75 minutes ($P=0.004$) as shown in FIG. 3.

Figure 4:
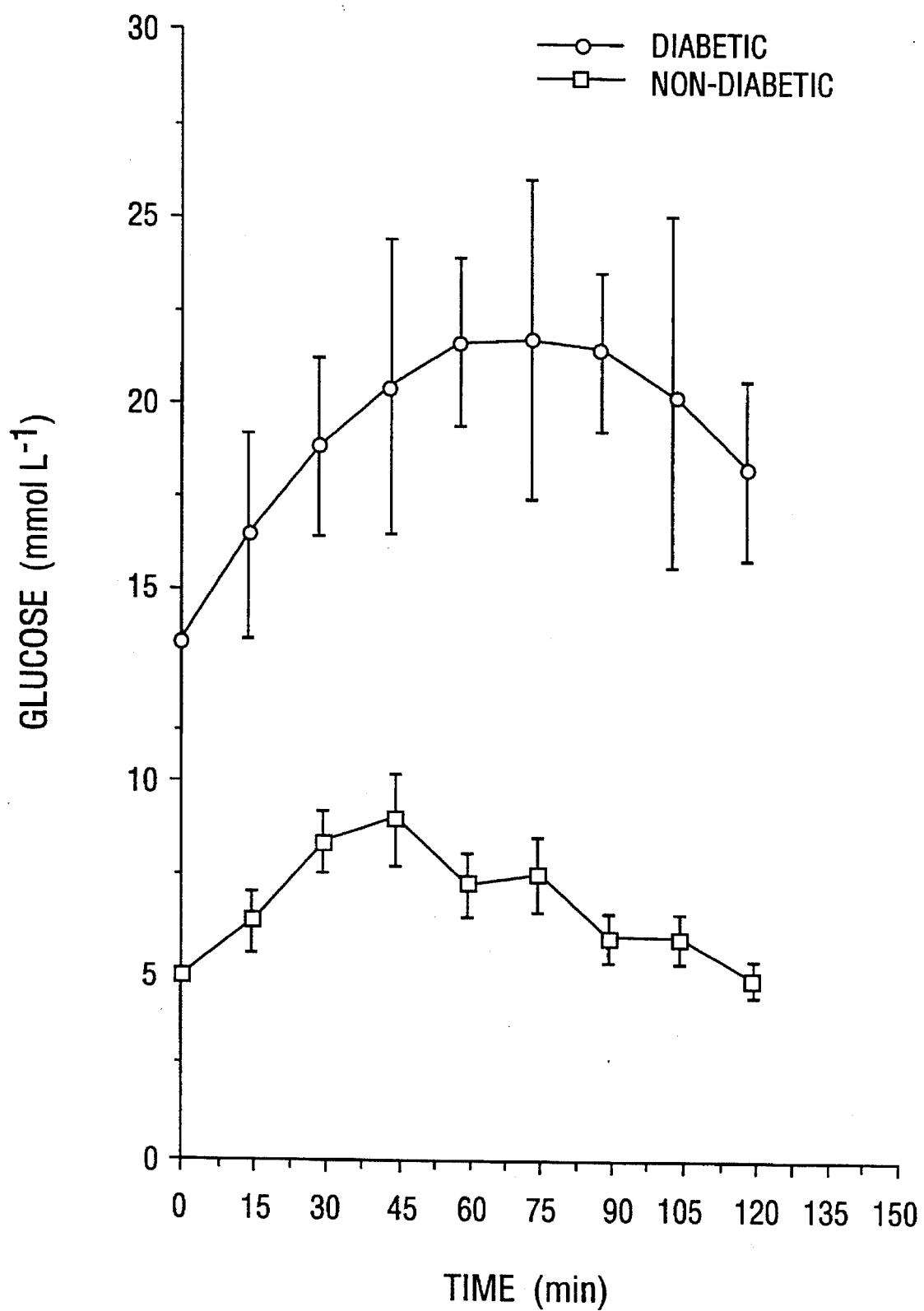
FIG. 4 compares plasma glucose levels between subjects with non-insulin dependent diabetes mellitus and controls at 15 min intervals up to 120 min.

The fasting glucose concentrations were significantly different between the subjects with NIDDM and non-diabetics ($P=0.009$). The glucose concentrations also were different between diabetics and non-diabetics at 15 min intervals as shown in FIG. 4. At other times post ingestion, glucose concentration was not measured on all subjects.

The area under the glucose concentration curve during the first hour, representing an overall time-weighted average, for the subjects with NIDDM was 252% of the area under the curve for the non-diabetics ($P=0.006$). The area under the curve during the two hours for the subjects with NIDDM was 292% of the area under the curve for the non-diabetics ($P=0.003$). Even though the subjects with NIDDM had more rapid gastric emptying, their plasma glucose peak was delayed (60–75 min) when compared to the normal controls (45 min).

The average rate of calories emptied into the intestine (calculated using the time of half gastric emptying) by the subjects with NIDDM was 3.1 kcal/min, while non-diabetic controls emptied at a rate of 1.6 kcal/min. The extremes in caloric emptying varied between a diabetic subject emptying at a rate of 7.1 kcal/min and a non-diabetic subject emptying at 1.2 kcal/min.

EXAMPLE 2

This example illustrates that gastric emptying could be controlled in Type II diabetics by intravenous administration of cholecystokinin and that the increased CCK levels were associated with normalization of several parameters of glucose metabolism, including insulin and blood glucose levels, GIP and hemoglobin AIC levels.

Control of Gastric Emptying by Administration of CCK

Seven subjects with early NIDDM (diagnosed for less than 2 years) underwent two separate gastric emptying studies. Subjects were five men and two women ranging in age from 33 to 49 and previously diagnosed as diabetic according to current WHO criteria using a 75 g glucose tolerance test (OGTT) with blood sampled fasting and at 2 hr. All patients had been on oral hypoglycemic medication which was discontinued the evening prior to the study. All studies were begun between 7–8 am following a 12 hour fast.

An 18 gauge angiocatheter was placed in one antecubital fossa for blood drawing while another 18 gauge angiocatheter was placed in the other antecubital fossa for a 0.9% (normal saline) infusion (60 ml/min). Gastric emptying studies utilizing a gamma camera (Scintronix USA, Inc., Woburn Mass.) were performed with a modified 0.62M (50 g glucose in 450 ml water) glucose solution. This solution has been used previously in gastric emptying studies (Schwartz, et al., 1990). Approximately 200 µCi of 99 metastable technetium sulfur colloid ($^{99m}$Tc-SC, CIS-US, Bedford, Mass.) was added and mixed with the glucose solution. The subjects drank the entire glucose solution within 5 min shortly after the $^{99m}$Tc-SC had been added to the solution.

The subjects were then seated at a 90 degree angle in front of a gamma camera. The subjects were instructed to stand at 10 min intervals so that anterior, posterior and left anterior oblique views could be obtained (one minute each) by the camera for a total of 120 min. Images were thus acquired every 10 min. The Scintronix gamma camera was used with a low-energy, all purpose collimator at a 20% window setting centered at 140 keV. The camera was connected to a Medical Data Systems Computer (Ann Arbor, Mich.). Counts in the stomach region of interest were calculated in each 60 second image. After correcting for radioactive decay, the count rates were converted to a percentage of the maximum count rate recorded.

Blood samples were drawn from the indwelling 18 gauge angiocatheter in the antecubital fossa at 15 min intervals beginning just prior to ingestion of the glucose solution and ending at 120 min. Blood for glucose evaluation was collected in grey-top vacutainer tubes containing potassium oxalate and sodium fluoride. Blood for insulin and C-peptide was collected in red top tubes. Samples for hemoglobin A-1-C, gastric inhibitory polypeptide (GIP) and CCK were collected in lavender top tubes containing EDTA. All glass tubes were from Becton Dickinson Vacutainer Systems, Rutherford, N.J. Glucose analysis were performed on a Paramax instrument (Baxter Healthcare Corp., Irvine, Calif.). Hemoglobin A1C was performed by the micro column test (Bio-Rad, Hercules, Calif. 94547).

The C-peptide assay was performed by Smith Kline Bioscience Laboratories, Van Nuys, Calif. by radioimmunoassay (Diagnostic Products, Los Angeles, Calif. 90045). The assay for insulin was performed by Smith Kline Bioscience Laboratory, St. Louis, Mo. by radioimmunoassay (Pharmacia Diagnostics, Fairfield, N.J. 07004). Assays for GIP and CCK were performed by radioimmunoassay by the Gastroenterology Unit at Mayo Clinic (Rochester, Minn. 55905) using in-house kits.

In the first test each subject drank the glucose solution. A gastric emptying study was then performed with simultaneous infusion of normal saline during a two hour period.

The second study was performed 3 days later. Subjects drank the glucose solution and a gastric emptying study was performed with simultaneous infusion of CCK (Kinevac™, Squibb Diagnostics Princeton, N.J. 08543) at 48 pM/kg/hr.

Both the saline and the CCK solutions were infused using an Abbott/Shaw Life Care™ Pump, Model 4 (Abbott Laboratories, North Chicago, Ill. 60064). The saline and CCK solutions were delivered by the pump through a vented Abbott/Shaw IV, Lifecare™0 pump set (Abbott Hospitals, Inc., North Chicago, Ill. 60064). The pump was set to deliver 60 ml fluid per hr. The infusate of CCK solution consisted of 3 vials of lyophilized CCK (5 µg each) rehydrated with 5 ml normal saline each. A total of 135 ml of normal saline was added to the rehydrated CCK for a total of 150 ml. The 150 ml was injected into an Empty Evacuated Container (Abbott Laboratories, North Chicago, Ill. 60064).

Infusions of the saline solution for the first test and the CCK solution for the second test were begun 10 min prior to ingestion of the glucose solution.

At the initiation of the study, blood was obtained for determination of hemoglobin A1C levels and C-peptide levels in five of the seven subjects. Results are show in Table 1.

TABLE 1

| Subject | Hemoglobin A1C % | C-Peptide % |
|---------|------------------|-------------|
| 1 | 4.3 | 4.0 |
| 2 | 9.0 | 2.9 |
| 3 | 4.8 | 3.6 |
| 4 | 9.5 | 4.5 |
| 5 | 8.3 | 6.6 |

Figure 5:
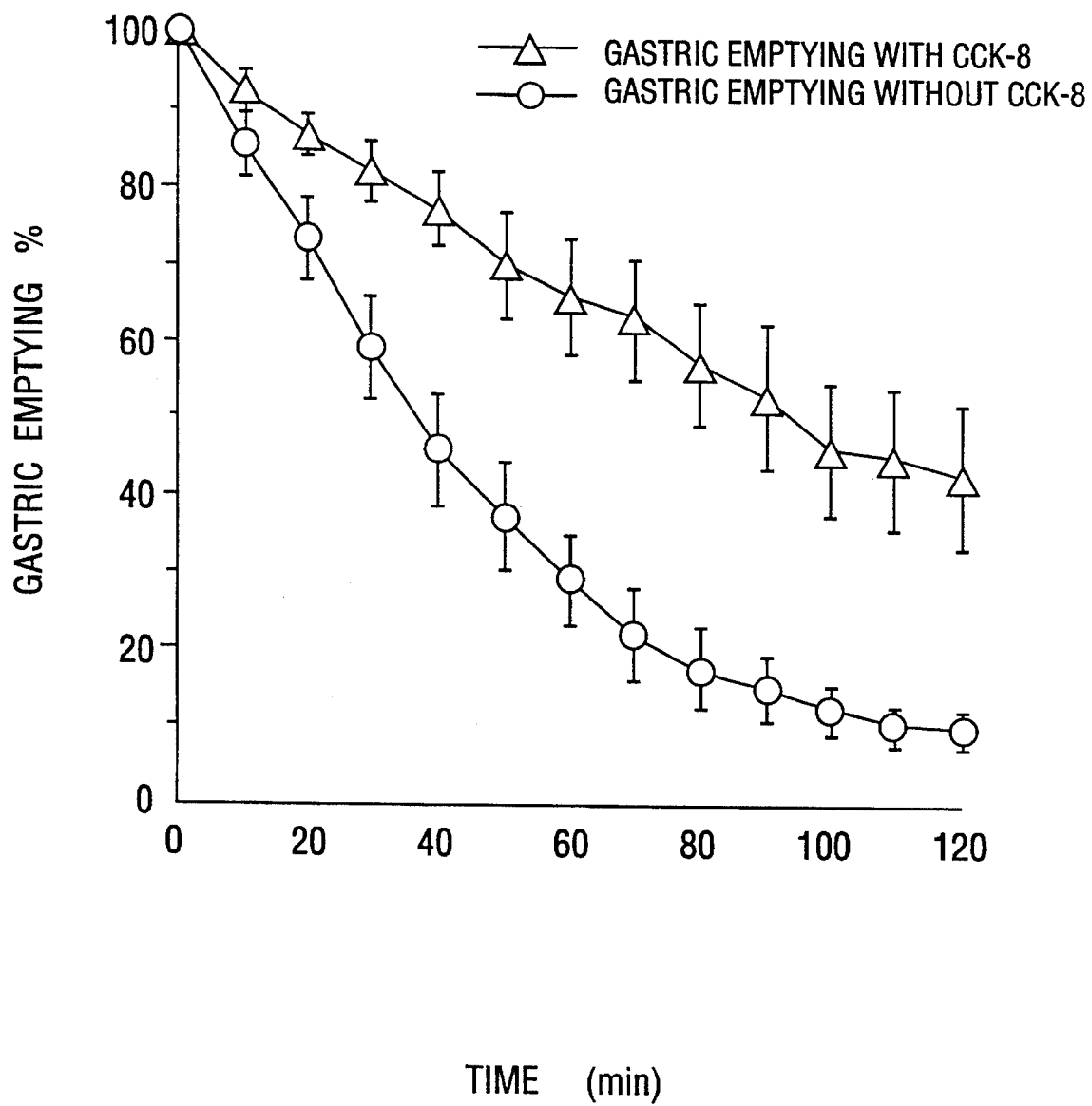
FIG. 5 shows gastric emptying time with and without administration of CCK-8 in diabetics.

The respective gastric emptying patterns with and without the simultaneous CCK-8 infusion are shown in FIG. 5. The gastric half-emptying time was more than doubled when CCK-8 was administered (with CCK, average=94.2 min, SE=12.3; without CCK8 average=40.9 min, SE=6.2; P=0.0042). The average area under the gastric emptying curve during the 2-hr period representing an overall time-weighted average when patients received CCK-8 was 175% of the average area under the curve for the same patients when not receiving CCK-8.

Figure 6:
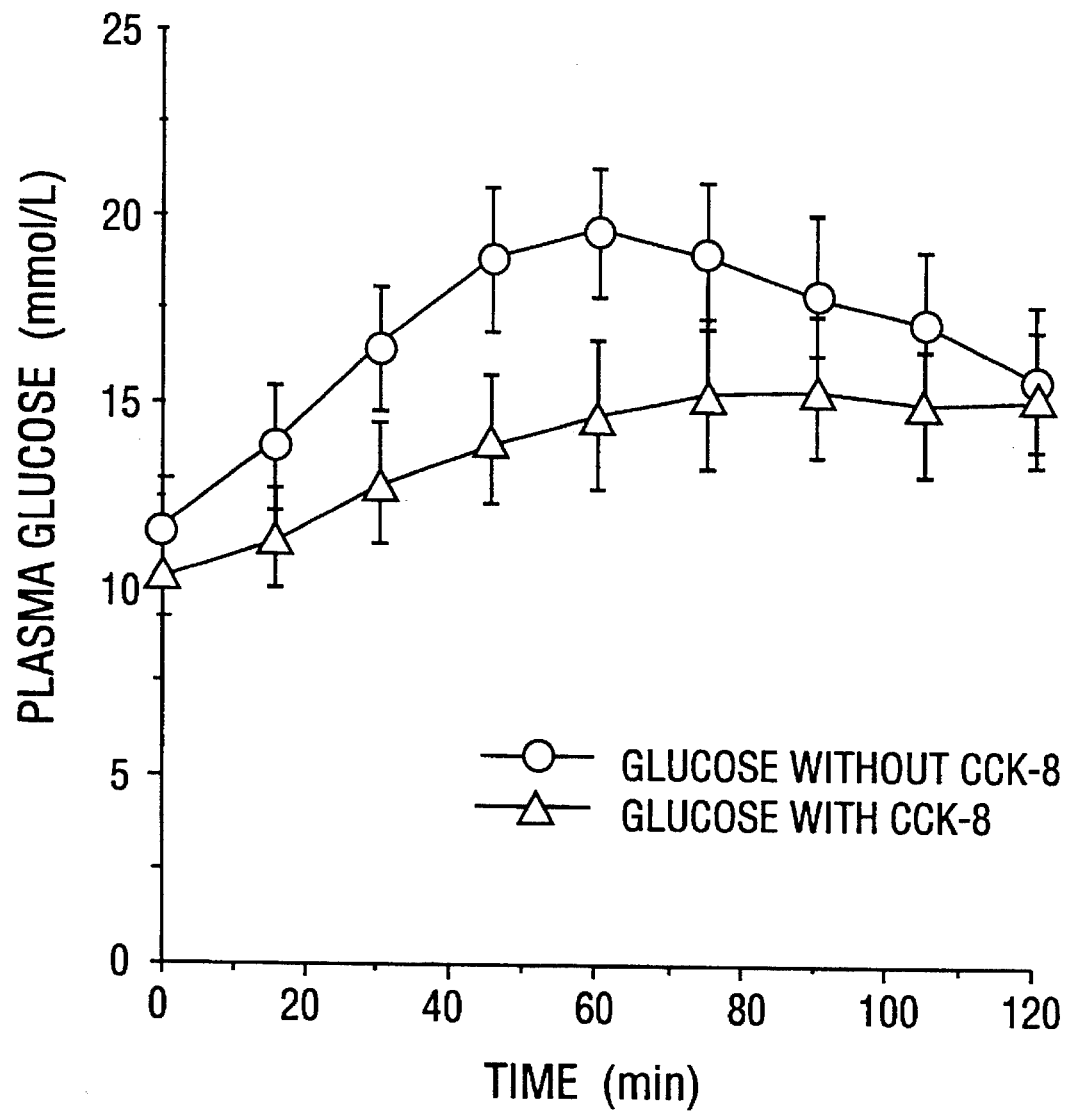
FIG. 6 shows mean glucose concentrations in diabetics with and without CCK-8 administration.
Figure 7:
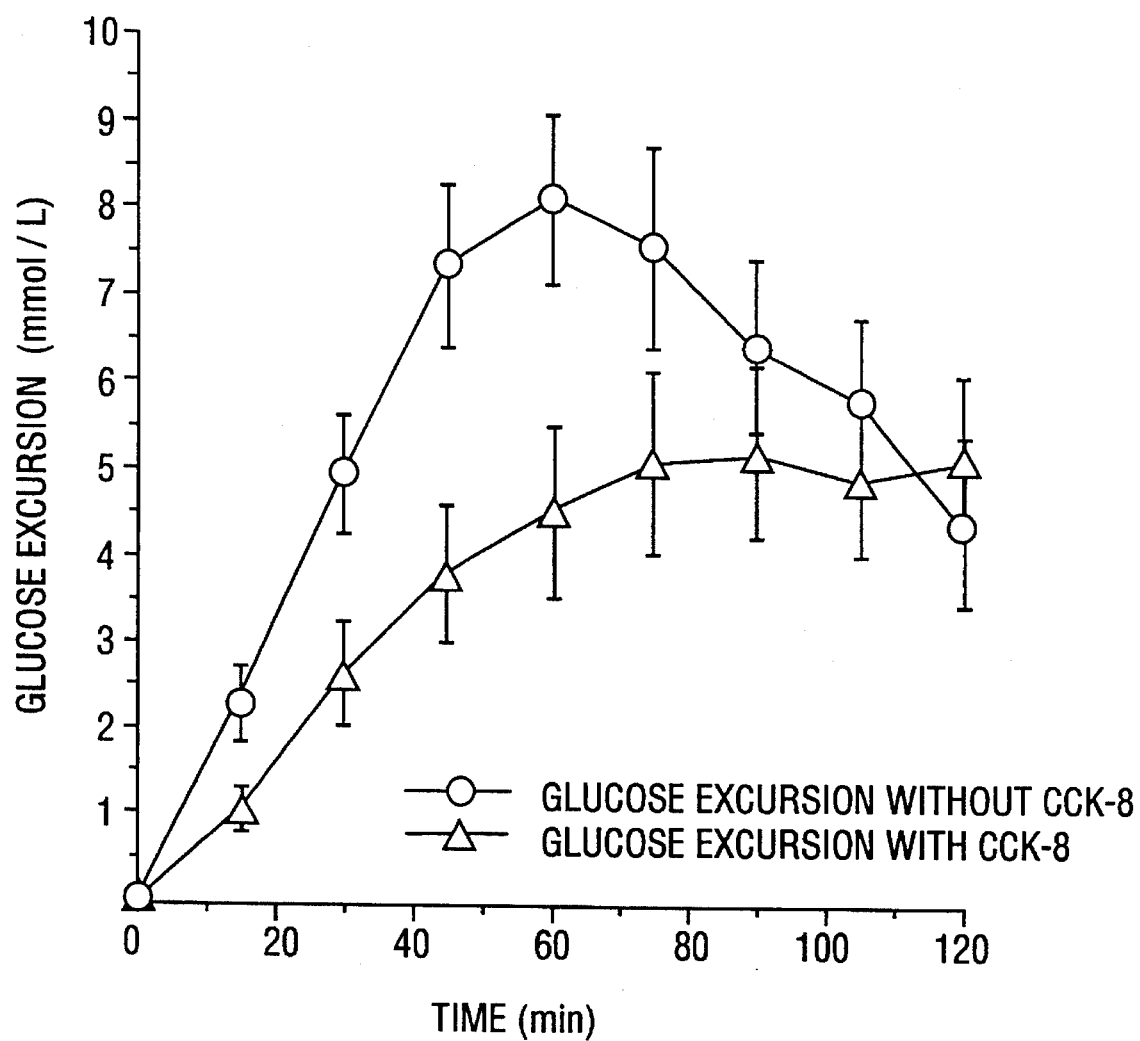
FIG. 7 shows mean glucose excursion values in diabetics with and without CCK-8 administration.

The mean glucose concentrations are shown in FIG. 6 and the mean glucose excursion values are shown in FIG. 7. The average glucose concentrations during the 2-hr period following ingestion of the glucose meal was lower when patients received the CCK-8 infusion than when they received a saline infusion (with CCK-8, average 14.0 mmol/L, SE 1.7; without CCK-8, average =17.1, SE=1.7; P=0.0073). Average plasma glucose values were lower with CCK-8 infusion over the time period of the study. The average glucose excurion value during the 2-hr testing period when patients received the CCK-8 infusion was 66% of the average value when patients received the saline infusion (with CCK-8, average 3.7 mmol/L, SE 0.7; without CCK-8, average=5.6 mmol/liter, SE=0.7; P=0.0550). The glucose excursion values with CCK-8 were lower from 15 to 105 min.

Figure 8:
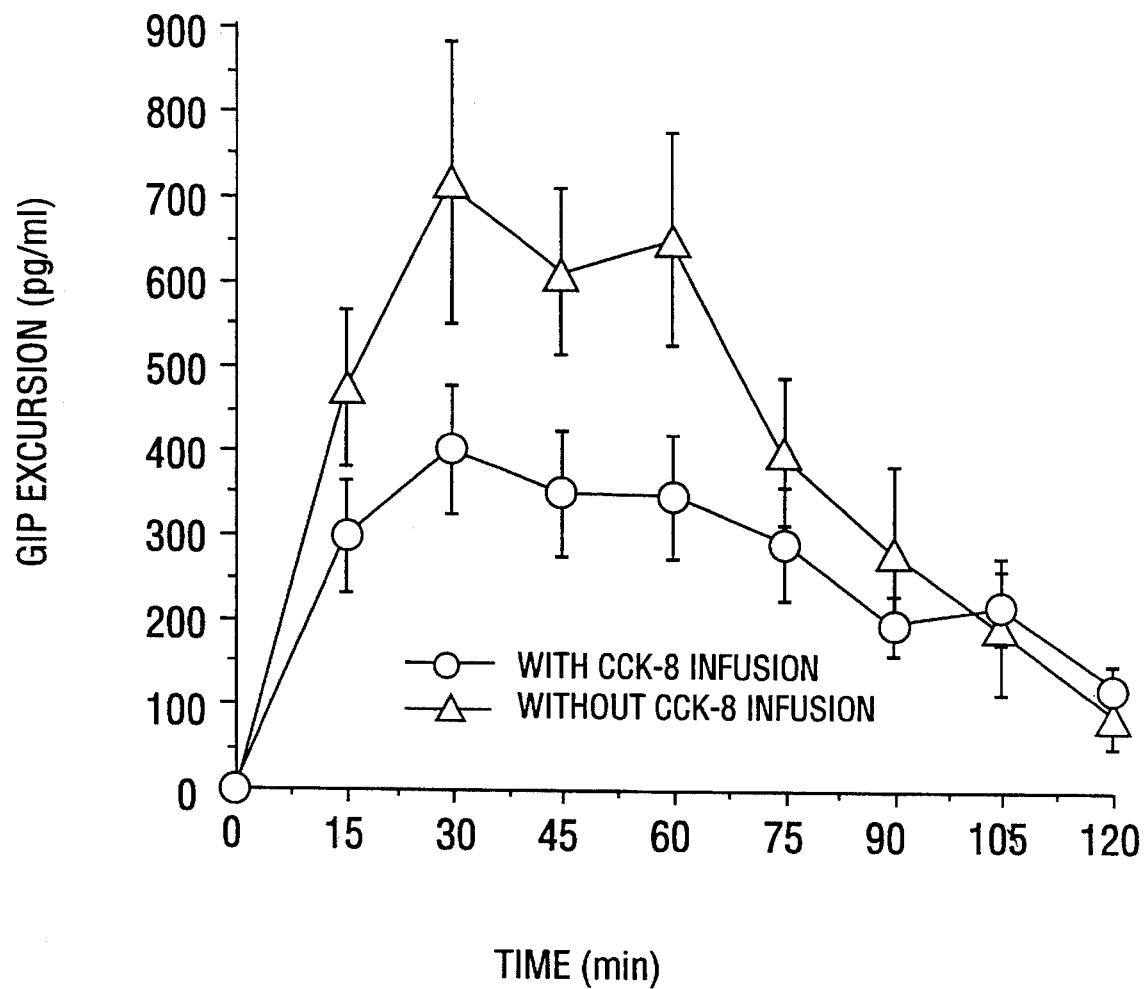
FIG. 8 compares mean GIP excursion values in diabetic patients with and without CCK-8 administration.

GIP excursion values with and without CCK-8 infusion are shown in FIG. 8. GIP excursion values were lower with CCK-8 infusion over most of the test period with the largest difference occurring 30–60 min after glucose ingestion. The average GIP excursion over the 2 hr period was lower when patients received the CCK-8 infusion (with CCK-8, average=266.4 pg/ml, SE=50.4; without CCK-8, average=420.4 pg/ml, SE=60.8; P=0.0032).

Figure 9:
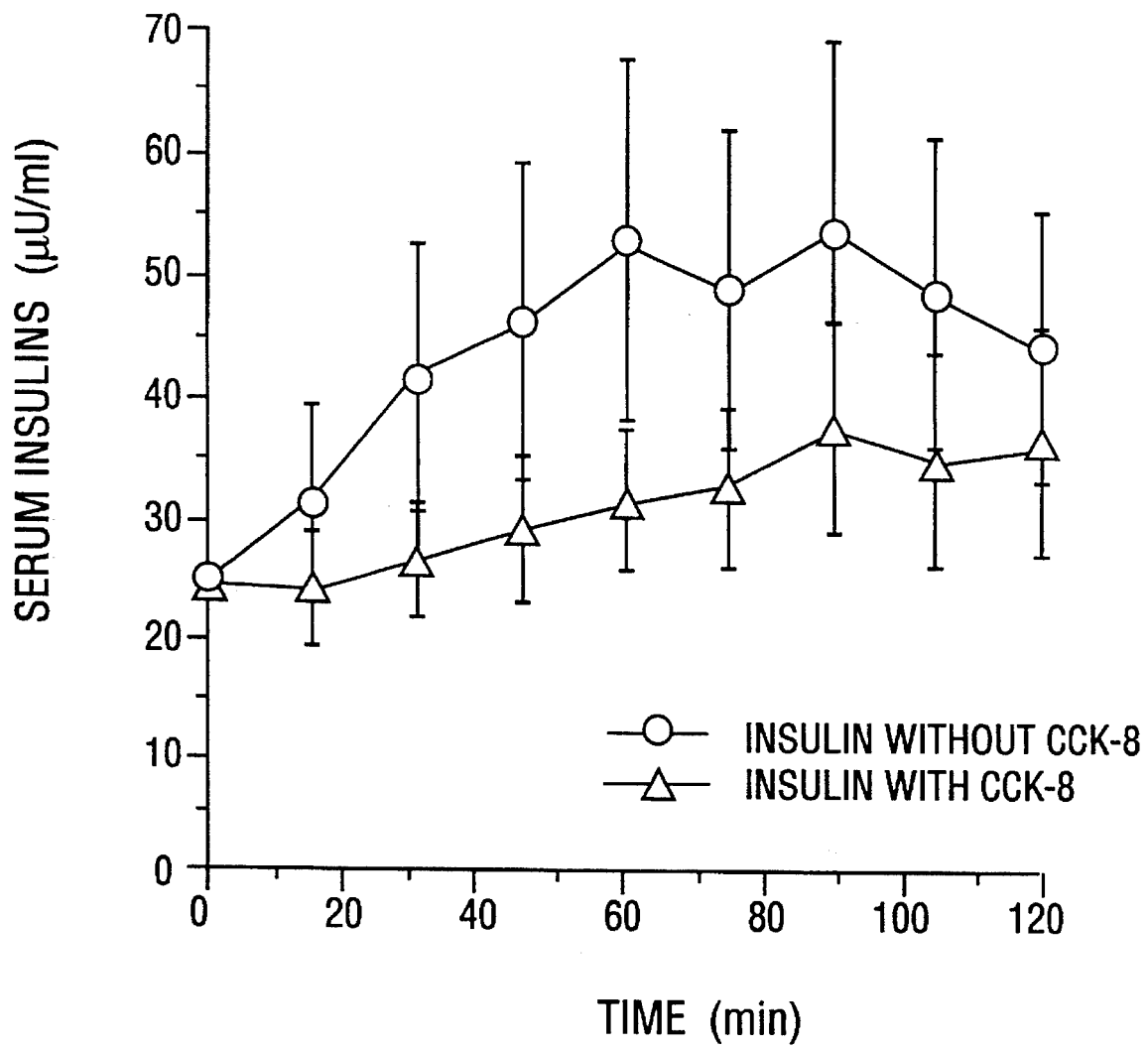
FIG. 9 shows serum insulin values in diabetic patients with and without CCK-8 administration.

Insulin concentrations (FIG. 9) were lower with CCK-8 infusion and the average value over the 2 hr period with CCK-8 infusion was 68% of the average value with saline infusion (with CCK-8, average=30.2 μU/ml, SE=6.2; without CCK-8, average=44.2 μU/ml, SE=11.7; P=0.1480) although the differences were not statistically significant.

Figure 10:
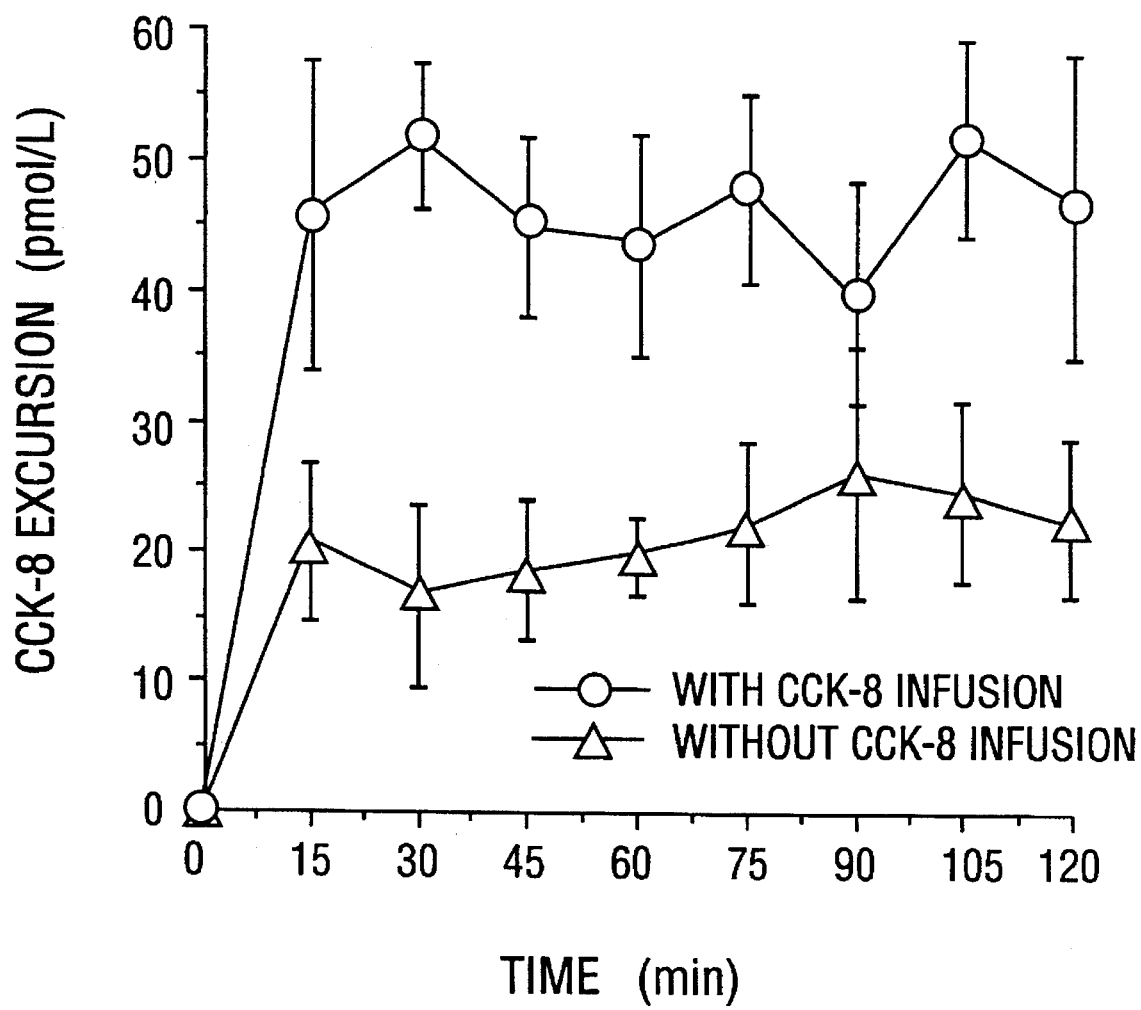
FIG. 10 shows changes in plasma CCK excursion values with and without administration of CCK-8.

The plasma CCK-8 excursion values are shown in FIG. 10. The average CCK-8 excursion was more than doubled during the CCK-8 infusion (with CCK-8, average=49.6 pmol/L, SE=5.6; without CCK-8, average=20.8 pmol/L, SE=6.1; P=0.0247). CCK-8 excursion values were higher in patients receiving the CCK-8 infusion from 15–120 min following the glucose ingestion compared to the same patients receiving only the saline infusion. Although at time zero CCK-8 had been infusing into the patients for a period of 10 min, no difference was noted in the CCK-8 levels between patients receiving CCK-8 compared with patients receiving the saline infusion at time zero (P=0.6667). This may be due to the initial small amount of CCK-8 that was being infused or it may have been due to adherence of CCK-8 to the plastic tubing. Even without the CCK-8 infusion, the CCK-8 excursion values following ingestion of the glucose solution were approximately 50% higher than the baseline (fasting levels) at all times (P=0.0765).

The initial mean concentration of the CCK-8 in the infusate was 29,200 pmol/liter. Following the 2 hr testing period, an average of 53,858 pmol/liter of CCK-8 was being infused. This increasing infusion level of CCK-8 appeared due to a significant adherence by CCK-8 to the plastic tubing during the initial portion of the study. Patients initially received 18.4 pmol/kg/hr, which gradually increased to 34 pmol/kg/hr over the course of the study. A similar finding by Liddle, et al. (1986) revealed that the CCK-8 infusion rate was actually 46% of the rate calculated from the amount of CCK-8 added to the infusion bottle, indicating that approximately half the CCK-8 had been lost in tubing and syringe. In this study, due to losses from absorption of the CCK-8 to the tubing, patients were initially receiving 33% of the CCK-8 added to the infusion bottle; by the end of the study, patients were receiving 61% of the CCK-8 concentration. This increasing concentration was likely due to saturation of the tubing by CCK-8.

None of the subjects reported any nausea or abdominal distress during the CCK-8 infusions. No adverse effects were reported or observed. The subjects did not perceive any differences in the effects of the CCK-8 compared with effects of the saline infusions.

EXAMPLE 3

Two diabetic subjects exhibiting rapid gastric emptying were treated by oral administration of a solution containing cholestyramine, a bile-binding resin. Results indicated that blood glucose was lowered after treatment and that gastric emptying was delayed.

Patients

Two recently diagnosed Type 2 diabetic subjects (diagnosed within 2 years) underwent 2 gastric emptying studies each. The first gastric emptying study involved drinking a 50 g oral glucose solution. The second gastric emptying study involved drinking the same 50 g oral glucose solution with the addition of 12 g of powdered cholestyramine mixed into the glucose solution. The subjects were 2 males 43 and 57 years of age. Both diabetic subjects were non-Hispanic whites. The subjects had been previously diagnosed as being diabetic using a 75 g oral glucose tolerance test (OGTT) with blood sampled fasting and a 2 hours according to current WHO criteria. No evidence of diabetic neuropathy or autonomic dysfunction was present in either of the diabetic subjects. Oral hypoglycemic medication, Micronase, 5 mg tablets twice a day, was taken by one subject as usual the evening before each study and the morning of each study. Neither of the subjects had a history of any recent surgical procedures and neither was taking any other type of prescribed or over-the-counter medication.

Gastric Emptying Studies

Gastric emptying studies utilizing a gamma camera (Picker Corp., USA) were performed with a modified 0.62 mmol/1 (50 g glucose in 450 ml water) glucose solution. Each study was begun at approximately 7:30 a.m. and finished by 10:00 a.m. For the first study, approximately 200 uCi of 99 metastable technetium sulfur colloid ($^{99m}$Tc-SC, CIS-US, Bedford, Mass.) were added and mixed with the glucose solution. The subjects drank the glucose solution in its entirety in a five minute span shortly after the $^{99m}$Tc-SC had been added to the solution.

The subjects immediately had their stomachs imaged following ingestion of the solution and then every 15 minutes for a period of 2 hours. Between images, the subjects were placed in a sitting position. Images of the stomach were taken both anteriorly and posteriorly. Both of these views (the geometric mean) were used in calculating the subjects' gastric emptying. Data was collected every 15 minutes. Each anterior and posterior view was acquired for 60 seconds.

The Picker gamma camera was used with a low-energy, all purpose collimator at a 20% window setting centered at 140 keV. The camera was connected to a Pinnacle Computer, Medasys Corp. (Ann Arbor, Mich.). Counts in the stomach region of interest were calculated and drawn separately for each 60 second image. After correcting for radioactive decay, the count rates were converted to a percentage of the maximum count rate recorded.

The same procedure was followed for the second gastric emptying study for each subject except that 12 g of powdered cholestyramine (Questran®, Bristol-Meyers Co., Evansville, Ind.) was added to the oral glucose solution immediately prior to the addition of $^{99m}$Tc-SC and the ingestion of the solution by the subject.

Plasma Glucose

Plasma glucose samples were drawn at 15 minute intervals beginning just prior to ingestion of the glucose solution (fasting) and ending at 120 minutes. The subjects' blood samples were collected for glucose analysis in gray-top Vacutainer tubes containing potassium oxalate and sodium fluoride (Becton Dickinson Vacutainer Systems, Rutherford, N.J.). Glucose analyses were performed on a Paramax instrument (Baxter Healthcare Corp., Irvine, Calif.).

Figure 11:
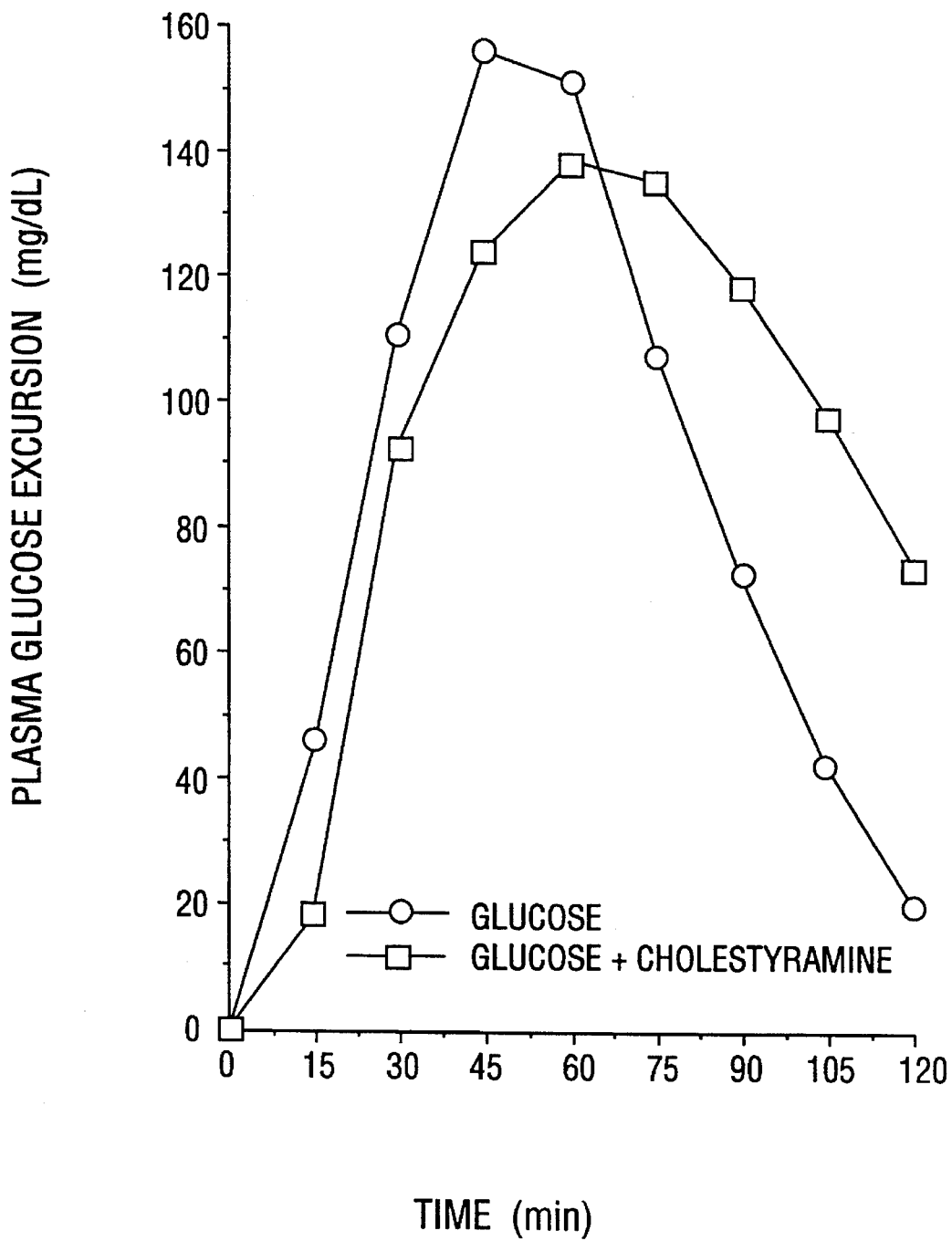
FIG. 11 is a graph showing plasma glucose excursion with and without administration of cholestyramine in diabetic subject number one.
Figure 12:
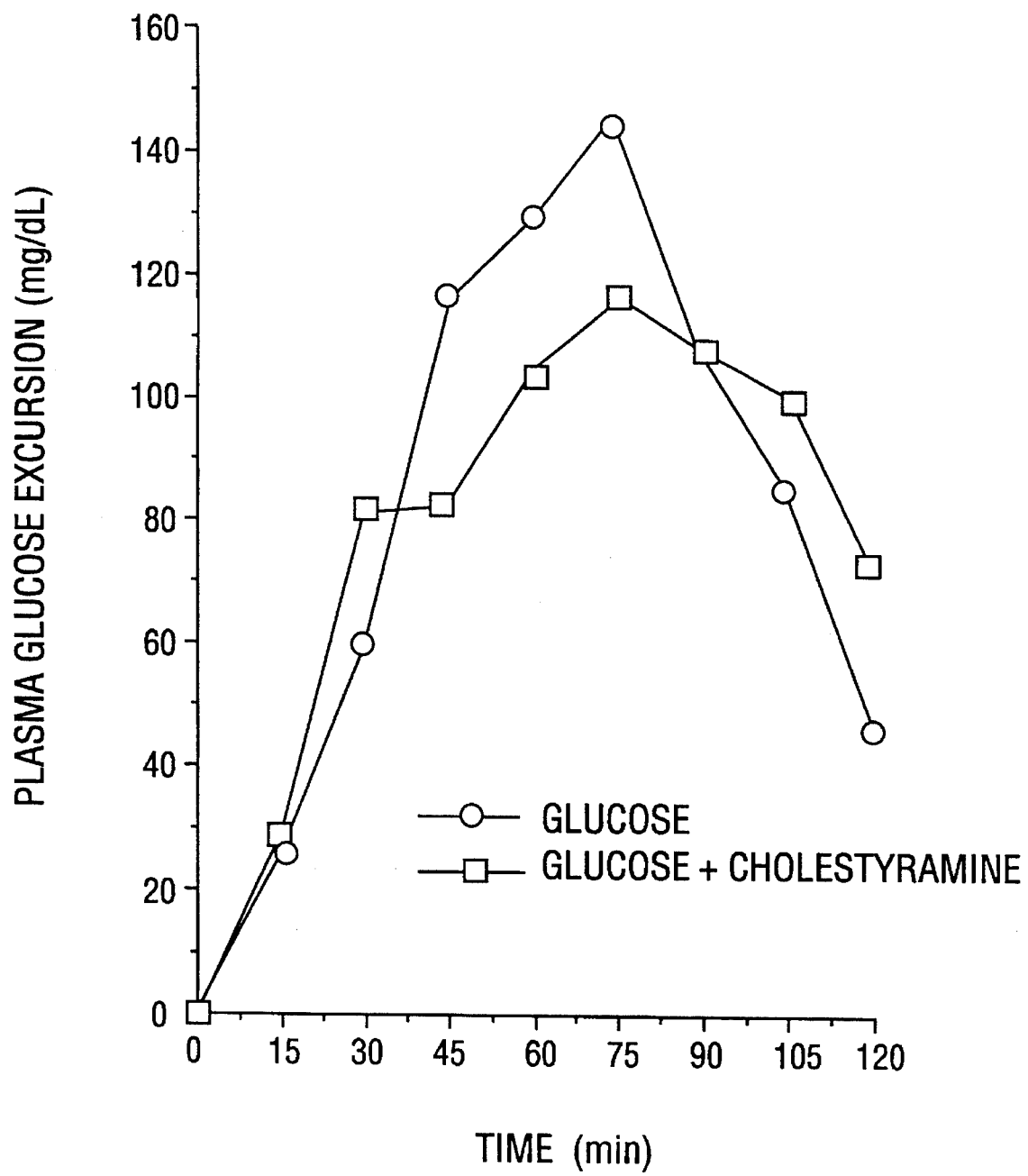
FIG. 12 is a graph showing plasma glucose excursion with and without administration of cholestyramine in diabetic subject number two.
Figure 13:
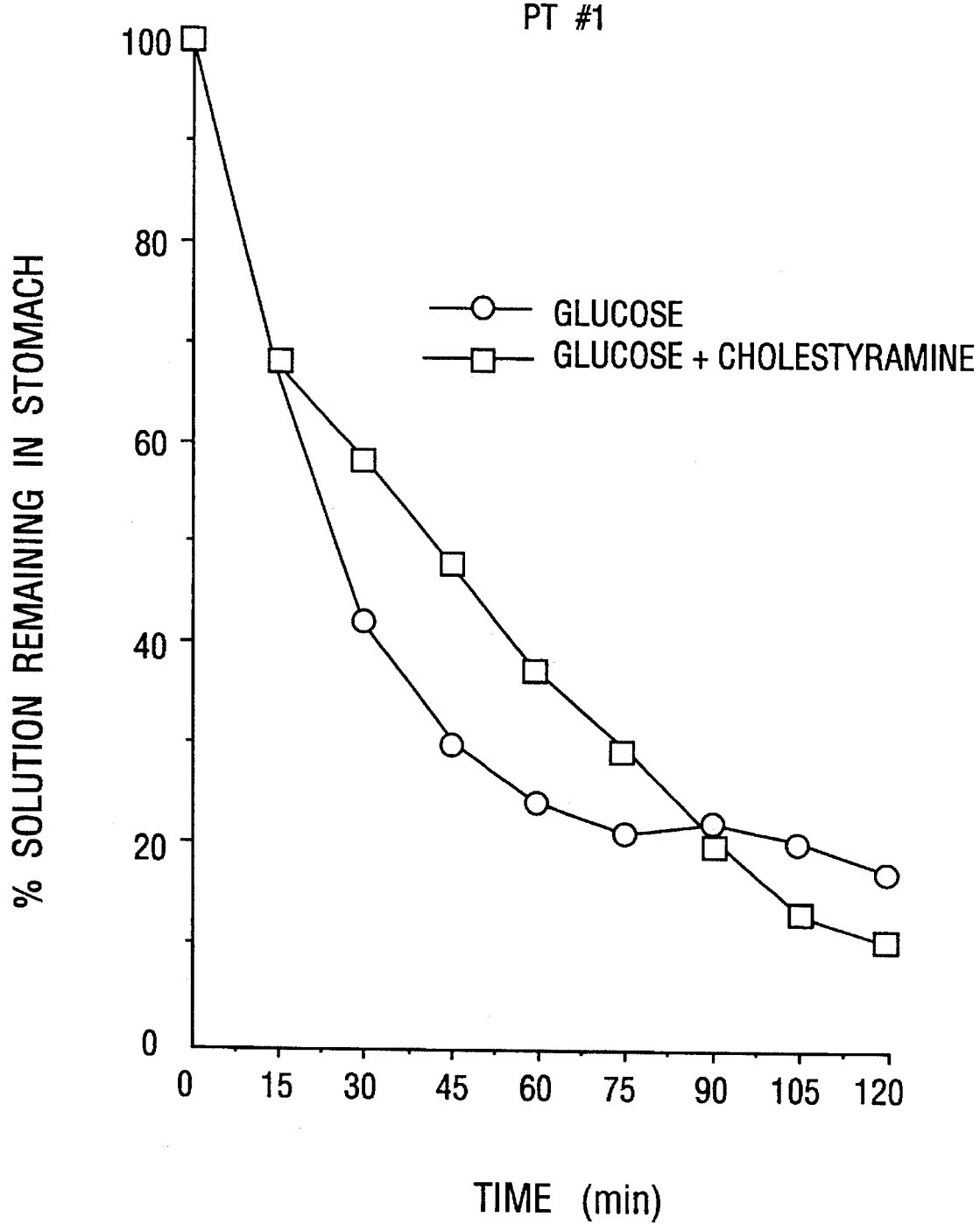
FIG. 13 shows gastric emptying with and without cholestyramine in diabetic subject number one.
Figure 14:
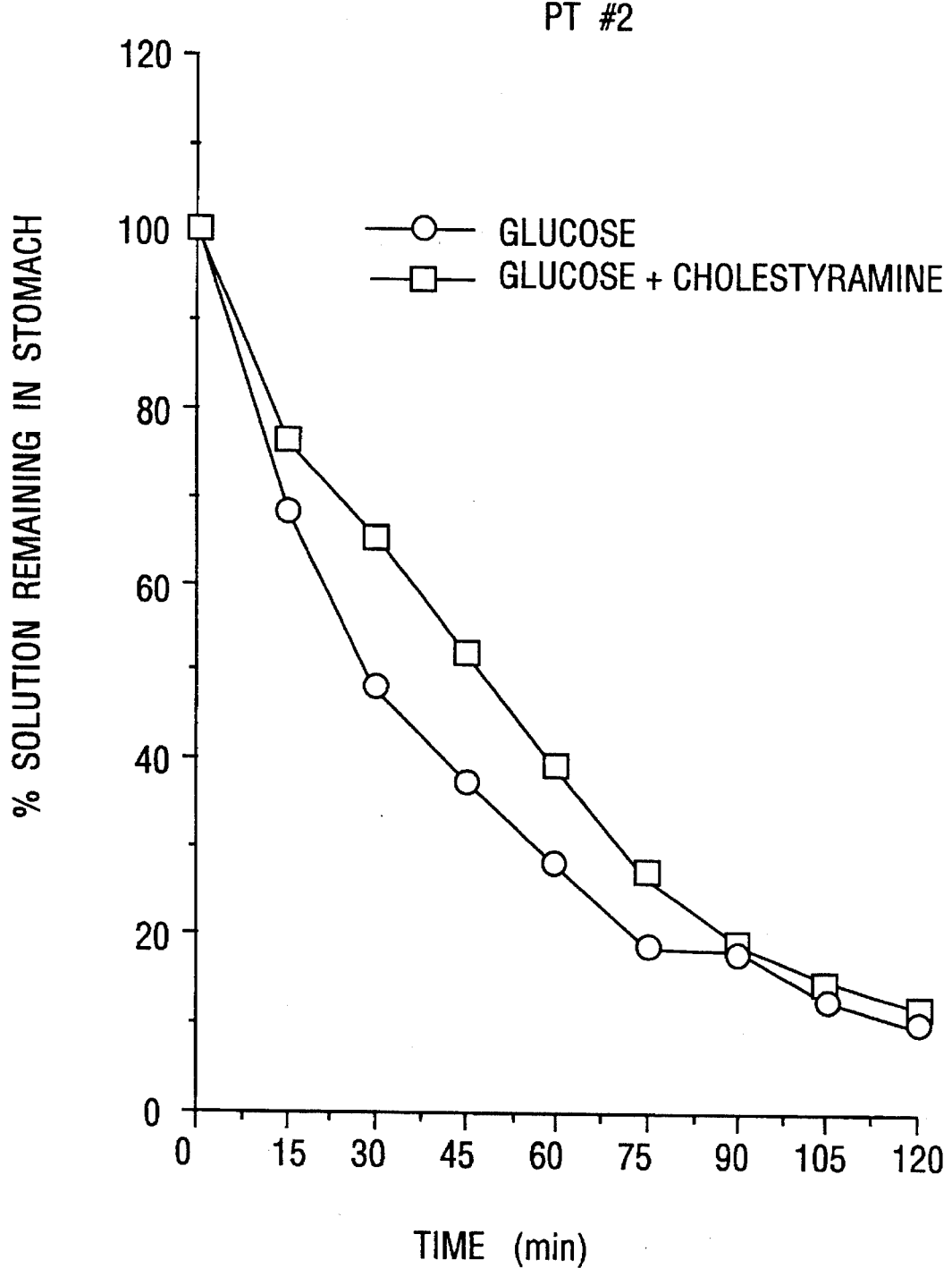
FIG. 14 shows gastric emptying with and without cholestyramine in diabetic subject number two.

Plasma glucose values were lower when cholestyramine was administered with the glucose solutions by comparison with administration of glucose alone, see FIGS. 11 and 12. Gastric emptying was also delayed in these subjects when cholestyramine was present in the glucose solution, as shown in FIGS. 13 and 14.

EXAMPLE 4

Figure 15:
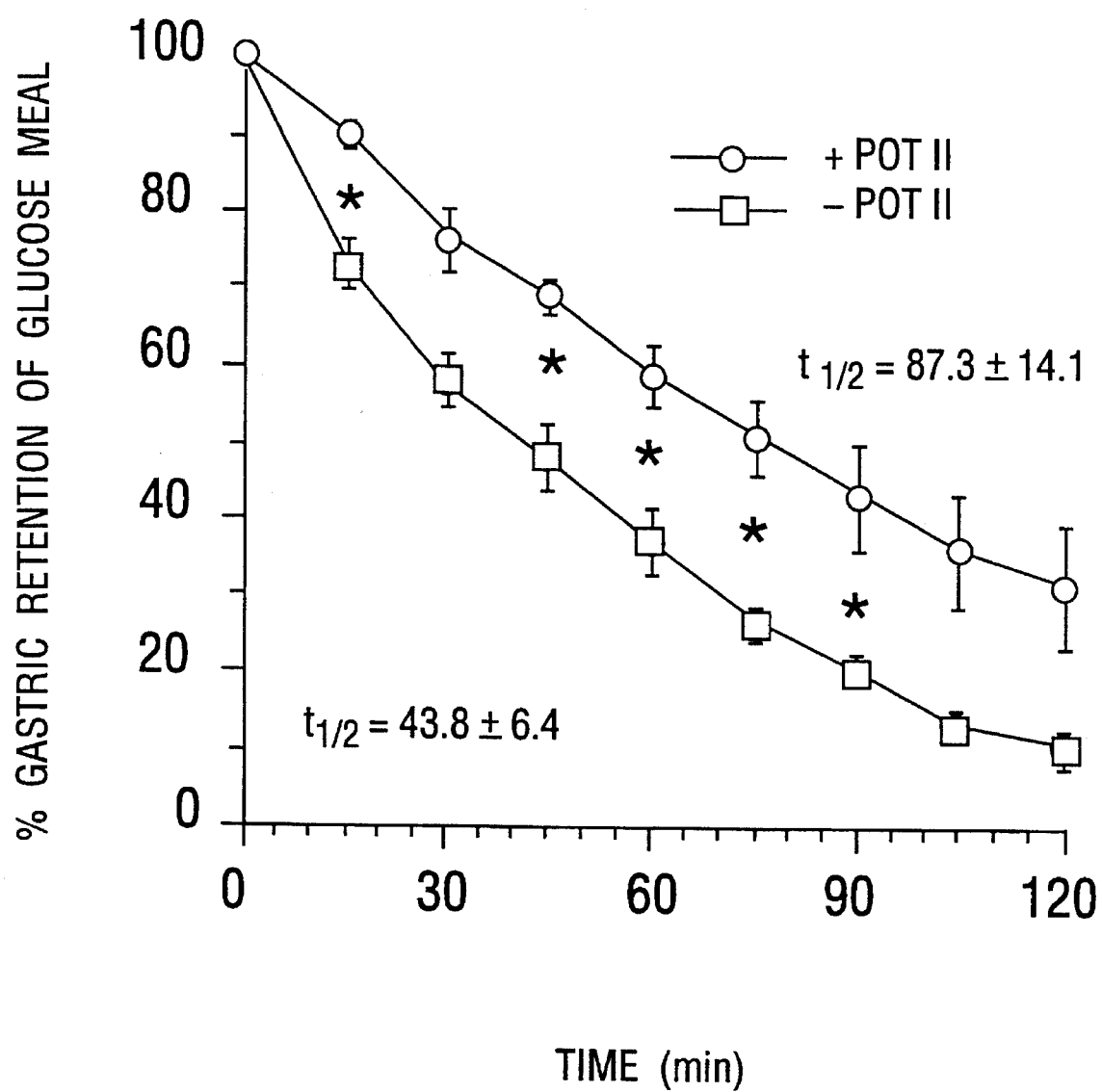
FIG. 15 is a graph showing gastric emptying in diabetic subjects with and without administration of POT II (n=4).
Figure 16:
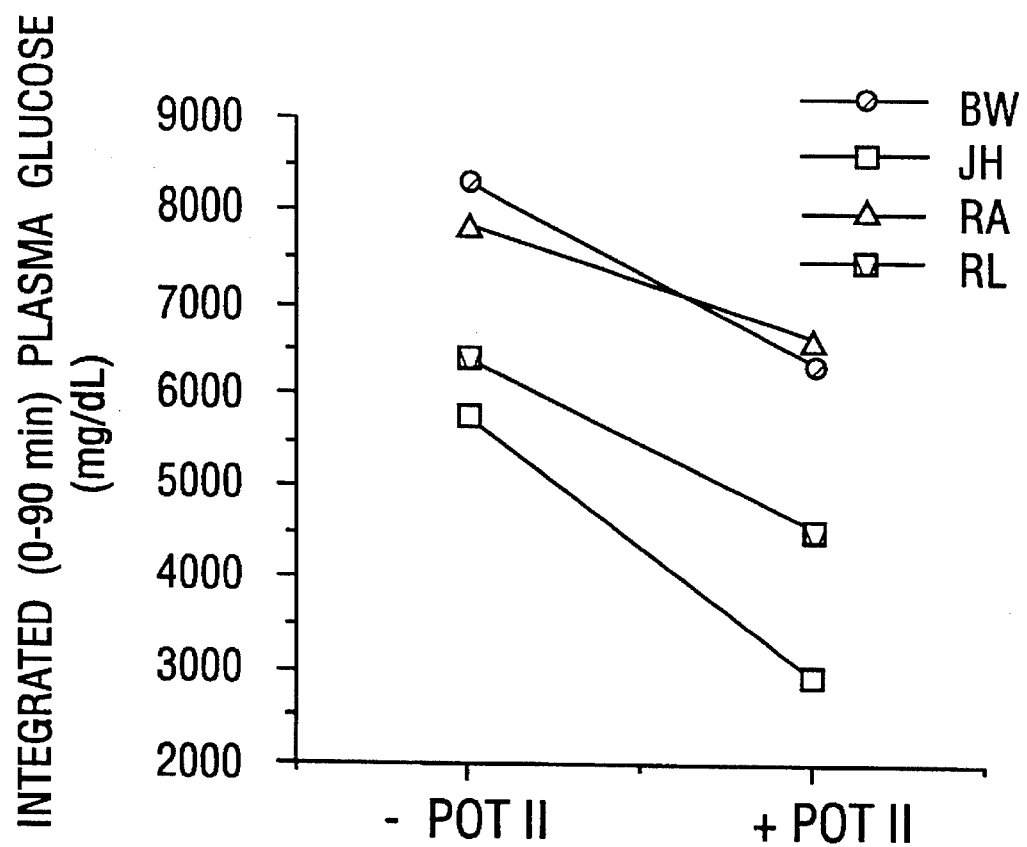
FIG. 16 shows integrated plasma glucose values in diabetic subjects with (+POT II) and without (−POT II) for n=4.
Figure 17A:
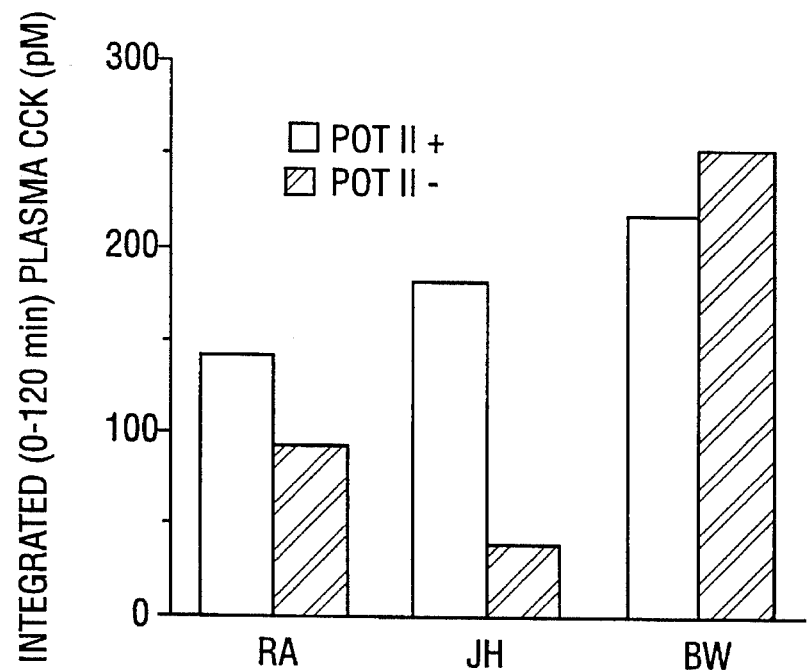
FIG. 17 shows integrated plasma CCK values in diabetic subjects with and without POT II: FIG. A, 0–120 min; FIG. B, 0–60 min.
Figure 17B:
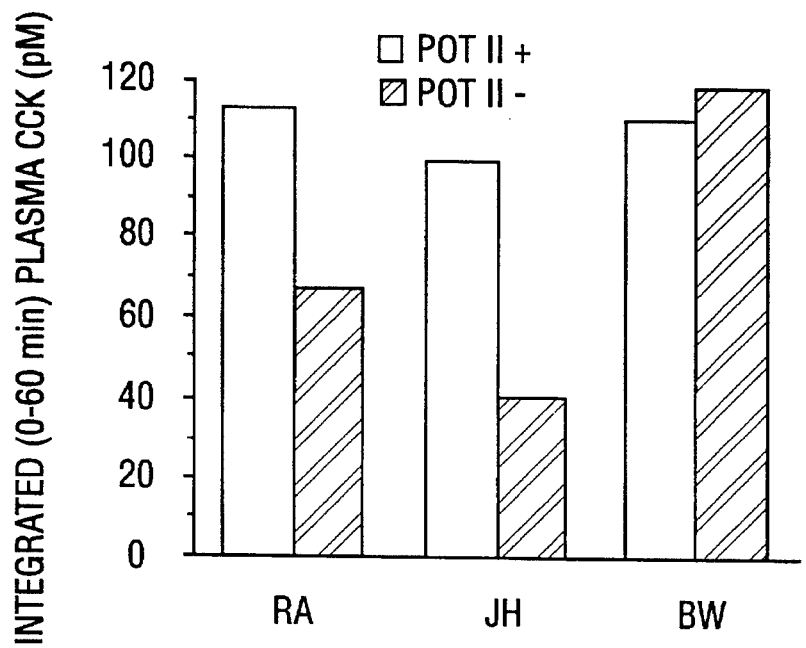

Further experiments confirmed that increasing plasma CCK levels was an effective means of controlling rapid gastric emptying and lowering high blood glucose and GIP levels. The effect of potato proteinase inhibitor II (POT II) on blood glucose and gastric emptying was tested in four diabetic subjects. The results showed that in all four of the subjects, POT II was effective in delaying gastric emptying (FIG. 15) and in lowering blood glucose levels (FIG. 16). In 2 of the 3 patients, POT II caused a marked increase in plasma cholecystokinin levels, compared to levels in the same patient not receiving the POT II (FIG. 17).

While this example illustrates the use of POT II, those of skill in the art will recognize that one might also employ Bowman-Birk inhibitor, a trypsin/chymotrypsin soybean inhibitor shown to stimulate pancreatic secretion of cholecystokinin in humans. This substance, like POT II, is not destroyed in the stomach, that is, is resistant to digestion. Bowman-Birk inhibitor is available as a trypsin/chymotrypsin inhibitor from soybean (Sigma Chemical Company, St. Louis, Mo.).

Gastric Emptying Studies

Gastric emptying studies utilizing a Nuclear Medicine Large Field of View gamma camera (Picker cor., USA) were performed using the two solutions (glucose+protein or glucose+protein+POT II). Each study was begun at approximately 7:30 a.m. and finished by 10:00 a.m. Each study was separated by at least one week. During each study, approximately 200 uCi of 99 metastable technetium sulfur colloid ($^{99m}$Tc-SC, CIS-US, Bedford, Mass.) were added and mixed with the liquid solutions. The subjects drank the solutions in there entirety within a five minute span immediately after the $^{99m}$Tc-SC has been added to the solution.

The subjects immediately stood up in front of the gamma camera and had their stomachs imaged following ingestion of the solution and then every 15 minutes for a period of 2 hours. Between images, the subjects were placed in a sitting position. Images of the stomach were taken both anteriorly and posteriorly. Both of these views (the anterior and posterior view=geometric mean) were used in calculating the subjects' gastric emptying. Data was collected every 15 minutes. Each anterior and posterior view was acquired for 60 seconds.

The Picker gammer camera was used with a low-energy, all purpose collimator at a 20% window setting centered at 140 keV. The camera was connected to a Pinnacle Computer, Medasys, Corp. (Ann Arbor, Mich.). Counts in the stomach region of interest were calculated and drawn separately for each 60 second image. After correcting for radioactive decay, the count rates were converted to a percentage of the maximum count rate recorded.

The same procedure was followed for the other gastric emptying studies for each subject except that 1.5 g of powdered POT II (Kemin Industries, Des Moines, Iowa) was added to the liquid solution immediately prior to the addition of $^{99m}$Tc-SC and the ingestion of the solution by the subject.

The diabetic subjects (diagnosed within 2 years) each underwent 2 gastric emptying studies. One gastric emptying study served as the control study and involved drinking 450 ml of a 50 g oral glucose solution mixed with 20 g of protein. The protein source was derived from "Joe Weiders's Sugar Free 90-Plus" formula (Weiders Health and Fitness Inc, Salt Lake City, Utah). The protein in this formula is from calcium (sodium caseinate), milk protein isolate, and egg white protein. A measured amount of 22.68 g of Joe Weiders's protein powder was the equivalent of 20 g of protein.

The other gastric emptying study involved drinking the same 450 ml, 50 g oral glucose solution mixed with 20 g of protein plus the addition of 1.5 g of POT II mixed into the glucose solution. POT II is an extract made from raw potatoes. The composition of POT II is 70% by weight potato proteinase inhibitor II. The remaining 30% is carbohydrate remaining from the raw potato. The typical concentration of POT II in Russett Burbank potatoes is 500 mg/kg of raw potatoes. In order to consume 1 gram of POT II, it would require the consumption of 2 kg of raw potatoes. The native protein has a molecular weight of 23,000 daltons and is resistant to digestion, making it unlikely to be absorbed by the GI tract. It is available from Kemin Industries of Des Moines, Iowa in a highly purified form.

The order in which the liquid solutions were administered altered with each subject. For example, patient #1 received the control solution during his first gastric emptying study. During his second gastric emptying study, he received the solution containing the POT II. The administration of these solutions was reversed with the next subject. Both studies involved the ingestion of 280 kcal (200 kcal in the glucose solution and 80 calories from the protein powder).

Analysis of Blood

Plasma glucose levels, plasma gastric inhibitory polypeptide (GIP), plasma Cholecystokinin (CCK), and serum insulin concentrations were measured. Blood samples were drawn from an indwelling 18 gauge Angiocath® (Becton Dickinson, Sandy, Utah) that had been placed in the antecubital fossa following the signing of the consent form by the subject. Blood was obtained at 15 min intervals beginning just prior to ingestion of the liquid solution and ending at 120 min.

Glucose

The blood for glucose analysis was collected in vacutainer tubes containing potassium oxalate and sodium fluoride (Becton Dickinson Vacutainer Systems, Rutherford, N.J.). Glucose analysis was performed on a Paramax instrument (Baxter Healthcare Corp., Irvine, Calif.) using a hexokinase methodology.

GIP

Blood for GIP was collected in glass tubes containing EDTA. All glass tubes were from Becton Dickinson Vacutainer Systems. Blood samples for GIP were collected and were immediately centrifuged for 30 min, then separated and frozen until the time of assay. Assays for GIP were performed by RIA by the Gastroenterology Unit at Mayo Clinic (Rochester, Minn.) using in-house assays based on the work done by Kuzio et al. (1974). Standards for this assay were obtained from Peninsula Lab, Inc., Belmont, Calif. The RIA intra-assay variation for the GIP assay was 6%; 11% for the inter-assay variation. The sensitivity of the GIP assay is 10-503 fmol/tube. This assay is stated to have no cross-reactivity with CCK-33, methione-enkephalin, secretin, motilin, gastrin, human pancreatic polypeptide, C-peptide, neurotensin, substance P, and bombesin.

CCK

Blood for the CCK bioassay was collected in 5 cc syringes and poured immediately into iced heparinized tubes. These tubes were placed immediately into a refrigerated (4° C.) centrifuge and spun for 15 minutes at 10,000 rpm. Roger Liddle's method for measuring CCK levels using isolated pancreatic rat acini as a bioassay was performed. The materials and methods are as follows:

Materials

The following substances were purchased for the CCK assay: Cholecystokinin-octapeptide (CCK-8) from Peninsula Laboratories, Inc., Belmont, Calif.; chromatographically purified collagenase, Freehold, N.J.; minimal Eagles medium amino acid supplement from GIBCO, Grand Island, N.Y.; bovine serum albumin, fraction V from Calbiochemicals, La Jolla, Calif.; Amylase, type VI-B from porcine pancreas, from Sigma Chemical Co., St. Louis, Mo.; Procion yellow dye from Polysciences, Inc., Warrington, PA; D-glucose from Fisher Scientific Co., Fairlawn, N.J.; and L-glutamin from Nutrition Biochem., Cleveland, Ohio.

The buffer used to prepare the isolated rat pancreatic acini was modified Krebs-Henseleit bicarbonate buffer (KHB), enriched with minimal Eagle's medium amino acid supplement, and 0.1 mg/ml purified soybean trypsin inhibitor; this buffer was equilibrated to pH 7.4 with 95% $o_2$ and 5% $CO_2$.

Tris (hydroxymethyl) aminomethane Ringer (TR) was used as incubation buffer and contained 40 mM Tris (hydroxymethyl) aminomethane, 103 mM NaCl, 1 mM $NaH_2PO_4$, 4.7 mM KCl, 1.28 mM $CaCl_2$, 0.56 mM $MgCl_2$, 11.1 mM glucose 0.1 mg/ml soybean trypsin inhibitor, the aforementioned minimal Eagle's medium amino acid supplement, and 5 mg/ml bovine serum albumin (BSA). This buffer was equilibrated with 100% $O_2$ and adjusted to pH 7.4.

Isolated pancreatic acini were prepared from (180–200 g) female Sprague-Dawley rats, 1–2 wk postovariectomy by enzymatic digestion of pancreas with collagenase in KHB. Acini were then incubated with plasma extracts (singlicates) or standard CCK-8 concentrations (triplicates) for 30 min. at 37° C. Amylase released into the medium was assayed using procion yellow coupled starch as substrate. Amylase released, expressed as percentage of total amylase content, was compared to a dose-response curve for CCK-8 in order to calculate the cholecystokinin content of plasma expressed as CCK-8 equivalents.

Methods

Cholecystokinin was extracted from plasma by adsorption onto SEP-PAK cartridges previously washed with 7.5 ml of methanol and 20 ml of water. The cartridges were then washed again with 20 ml of water and the CCK was eluted with 1 ml of 100% ethanol/1% trifluoracetic acid (4:1, vol/vol). The eluants were collected in 30-ml flat-bottomed incubation vials and dried under a nitrogen stream at 45° C. These vials were subsequently used for incubation with 1-ml acini suspended in TR. Recoveries of CCK standards were measured by adding known amounts of CCK-8 to plasma from fasted rats. These plasma samples were then processed through SEP-PAK cartridges as described previously and assayed for CCK-like activity by comparing the bioactivity of plasma samples with those of standard curves of CCK-8. Concentrations of CCK-8 ranging from 3 to 100 fmol were added to plasma and yielded recoveries of 89.2%±5.72% (mean±SD, n-10) for CCK-8.

Insulin

Blood for insulin was collected in red-top glass tubes (containing no preservative). The blood collected for insulin analysis was centrifuged and the serum was poured off into plastic tubes and then immediately frozen until the time of assay. The assay for insulin was performed by Dr. Ralph DeFronzo's laboratory at The University of Texas Health Science Center using Diagnostic Products Corp. (Los Angeles, Calif.) radioimmunoassay (RIA) procedure. The RIA intra-assay variation for the insulin assay was 2%; 4% for the inter-assay variation. The sensitivity of the insulin assay is 1 µU/mL.

Patients

The subjects were 4 males 34, 43, 57, and 50 years of age, all recently diagnosed as Type 2 diabetics. Two of the subjects were non-Hispanic whites, two subjects were Hispanic. The subjects had been previously diagnosed as being diabetic using a 75 g oral glucose tolerance test (OGTT) with blood sampled fasting and at 2 hours according to current WHO criteria. No evidence of diabetic neuropathy or autonomic dysfunction was present in any of the diabetic subjects. Oral hypoglycemic medication, Micronase, 10 mg tablets twice a day, was taken by one subject as usual the evening before each study. No medication was taken by any of the other subjects. None of the subjects had a history of any recent surgical procedures.

Results

The effect of POT II on mean plasma glucose incremental values was to suppress the incremental postprandial plasma glucose rise. Baseline value for plasma glucose without POT II is 128 mg/dL; with POT II 135 mg/dL. Integrated (0–90 minutes) incremental glucose values were significantly decreased after oral administration of POT II (p=0.038) with each patient showing a substantial decrease (FIG. 16, n=4).

Figure 18:
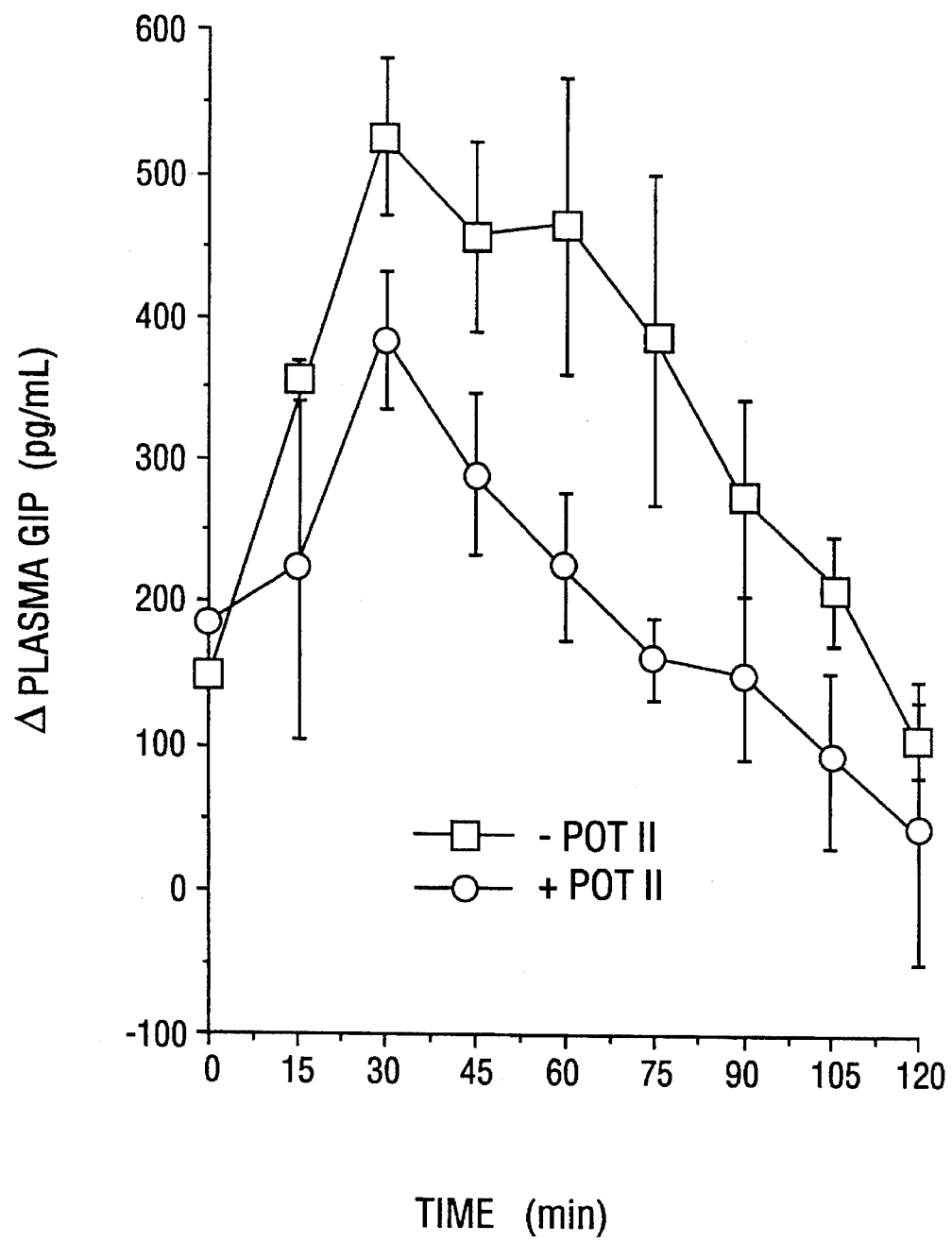
FIG. 18 shows the effect of POT II on plasma GIP concentration in diabetic subjects (n=3).

Effect of POT II on plasma GIP concentrations. POT II substantially suppressed the rise in plasma incremental GIP levels. Baseline value for plasma GIP without POT II was 148 pg/mL; with POT II 186 pg/mL. Integrated (0–120 minutes, FIG. 9) incremental GIP values were significantly decreased after oral administration of POT II (p=0.030) with all patients undergoing a decrease (FIG. 18, n=3).

Figure 19:
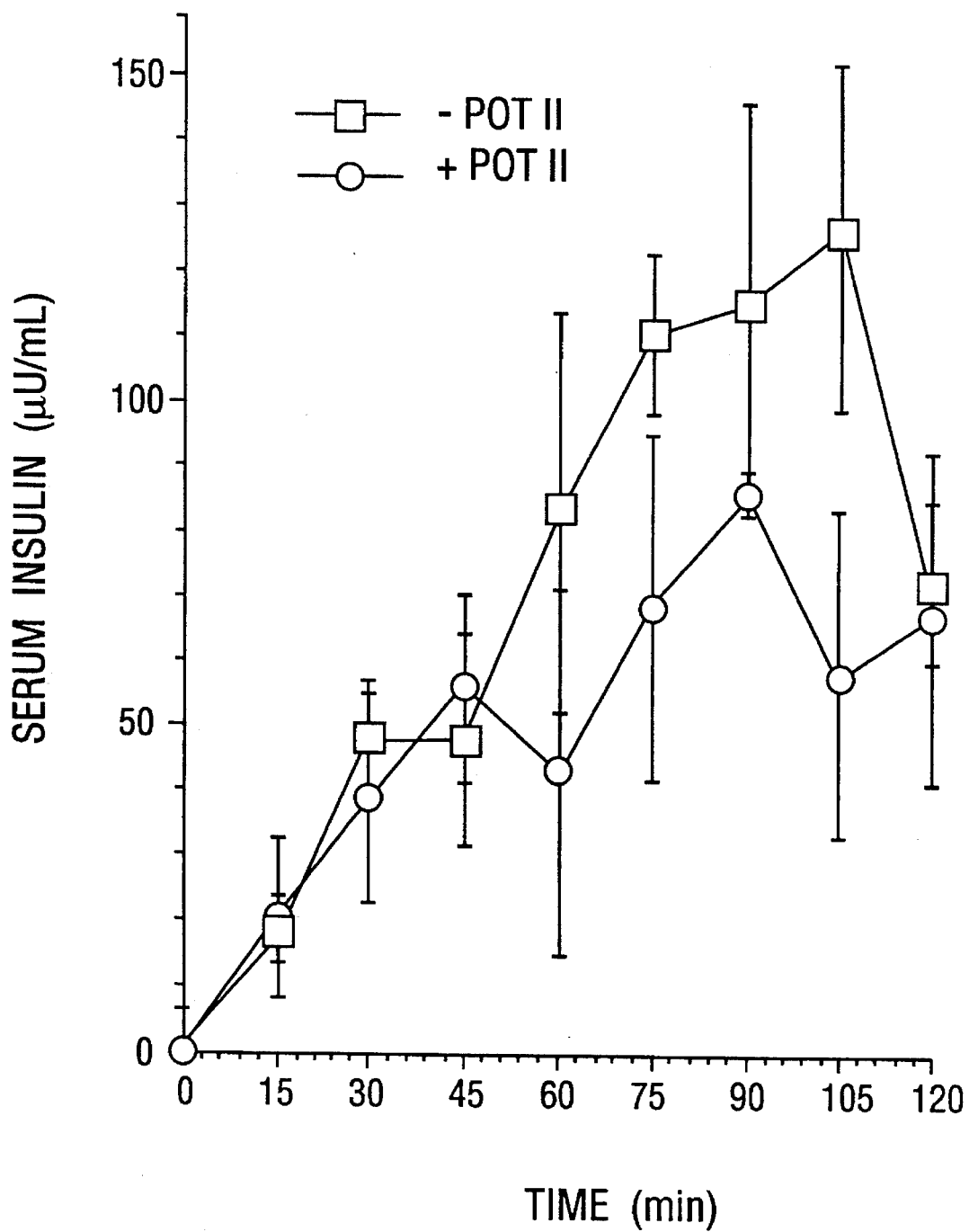
FIG. 19 shows the effect of POT II on serum insulin increment in diabetic subjects (n=3).

Effect of POT II on serum insulin values. The rise in incremental serum insulin after 45 minutes was suppressed by POT II. Baseline value for serum insulin without POT II is 23.25 µU/mL; with POT II 13.70 µU/mL. Integrated (0–120 minutes) incremental insulin values were decreased in all 3 patients after oral administration of POT II, (FIG. 19, n=3), although the differences did not attain statistical significance (p=0.140).

Effect of POT II on gastric retention of a liquid test meal. FIG. 15 shows that POT II significantly ($P<0.02$) slowed gastric emptying of the test meal. Mean gastric half-emptying times were 44 minutes without POT II and increased to 87 minutes with the addition of POT II. Integrating the values over the 120 minutes (area under the gastric emptying curve by trapezoidal rule) showed that each patient had a substantial increase in retention of the glucose meal when given POT II.

Figure 20A:
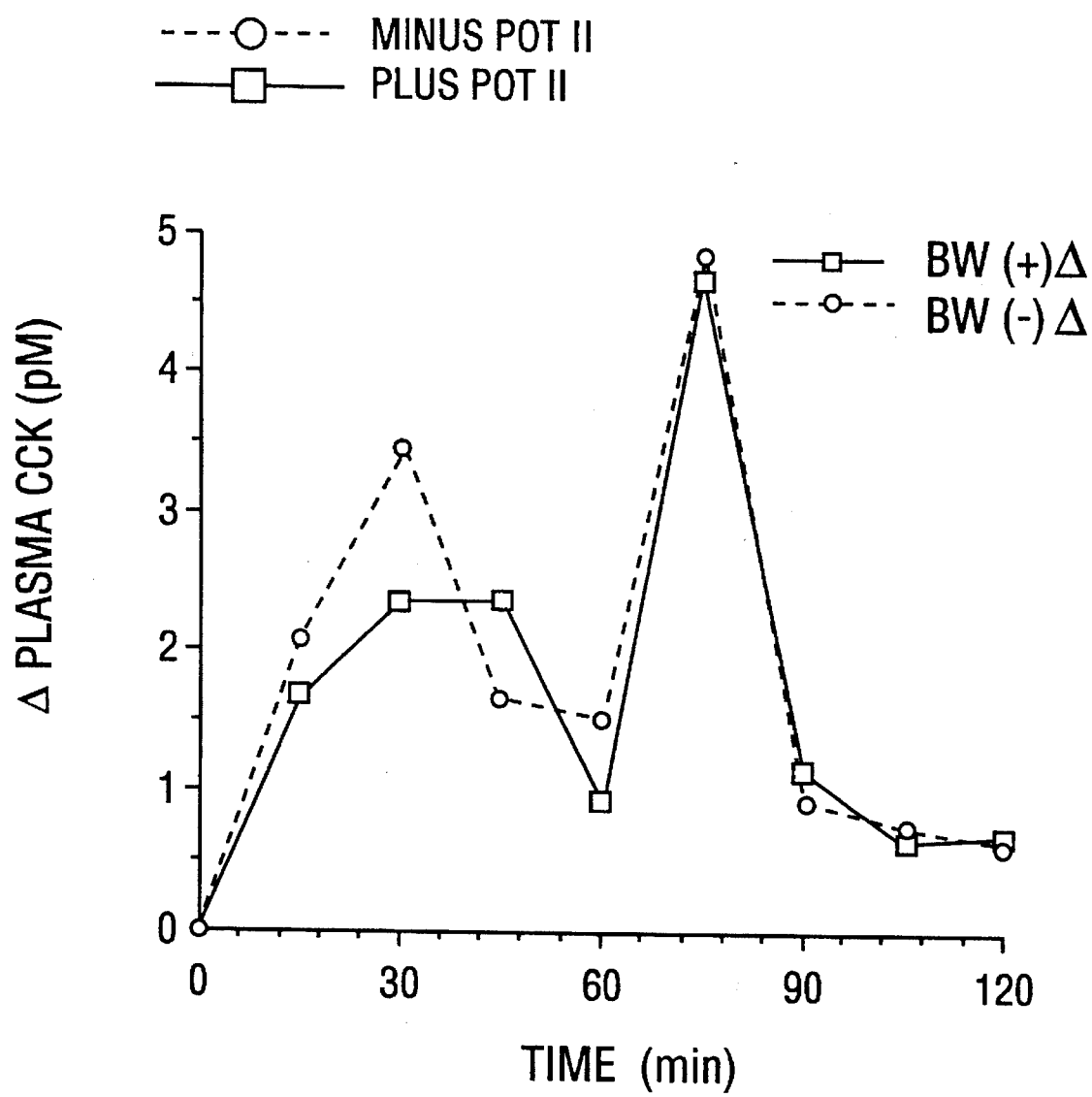
FIG. 20 shows incremental plasma CCK levels with respect to time in diabetic subjects with and without administration of POT II: Panel A is subject one; Panel B is subject two; and Panel C is subject three.
Figure 20B:
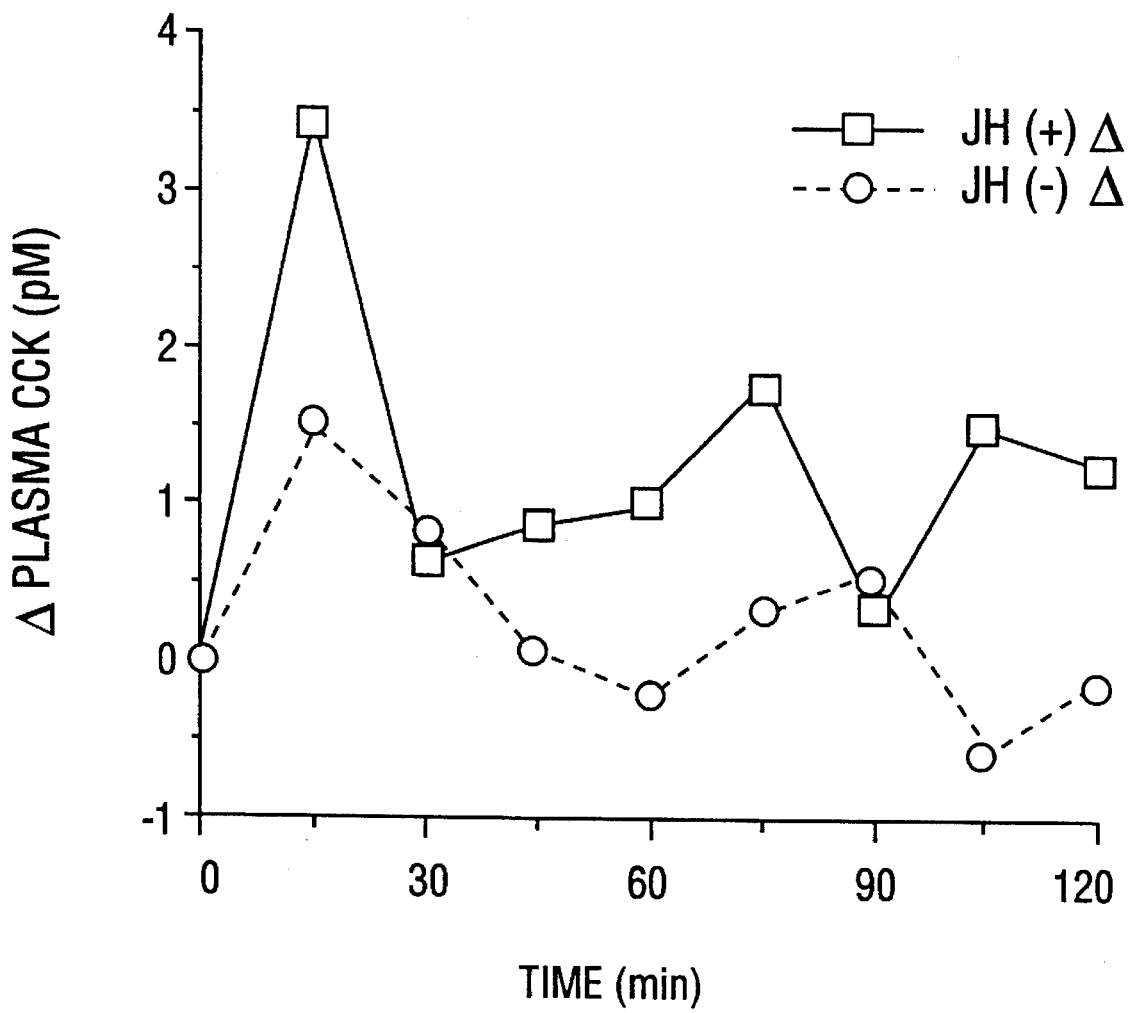
Figure 20C:
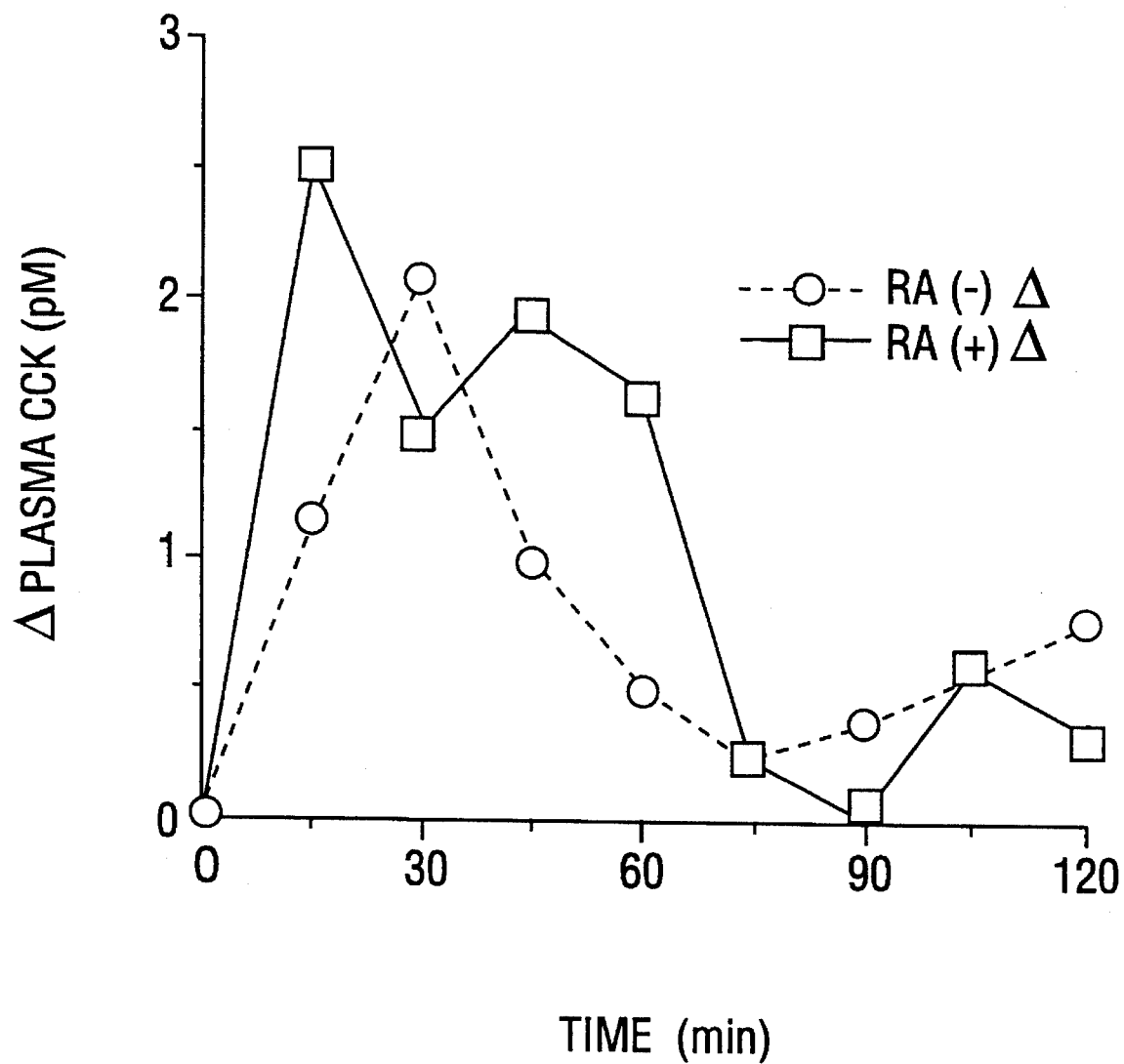

Effect of POT II on plasma CCK levels. Integrated (incremental) plasma CCK levels in two of three patients showed substantial increases when POT II was added to a test meal (FIG. 17). Incremental plasma CCK levels vs time (FIG. 20) show that two patients responded to POT II with substantially increased rises in plasma CCK during the first 60–90 minutes. It is unclear why one patient did not show an increase in plasma CCK with POT II, especially since his metabolic parameters (i.e., glucose increment, gastric emptying, insulin and GIP) all changed in the direction expected to occur with increased CCK release. The plasma CCK profile was atypical in that it showed a very marked biphasic response to both test meals and his integrated CCK response to the control meal (–POT II) was considerably higher than in the other two patients.

In summary, results showed that plasma CCK concentrations increased by 50% in 2 out of 3 patients who received POT II. Postprandial plasma insulin and glucose levels and rate of gastric emptying were significantly decreased in all 3 patients.

EXAMPLE 5

Some strains of Zucker rats are considered to be a model for type II diabetes. Such rats have a genetic propensity to become obese and to develop typical symptoms of diabetes such as elevated blood sugar. The inventors have shown that in this animal model for diabetes, rapid gastric emptying was associated with the diabetes and that gastric emptying could be slowed with consequent reduction in plasma glucose and a rise in plasma CCK levels.

Modulation of Accelerated Gastric Emptying in a Rat Model for Type 2 Diabetes

Eight male obese Zucker rats of a strain that becomes diabetic by 10 wks of age and 8 matched lean Zucker rats as controls were studied. After overnight fast, rats 10 wks old were fed by gavage a 30% glucose solution (1 mg/100 g body weight) containing 150 µCi of $^{99m}$Tc-SC. Each rat was tested with and without 1% camostat, a trypsin inhibitor known to stimulate CCK release, in the glucose solution. Gastric emptying was monitored by gamma scintigraphy at 10 min intervals. Fasting and 1 hr postprandial plasma glucose were determined.

Figure 21:
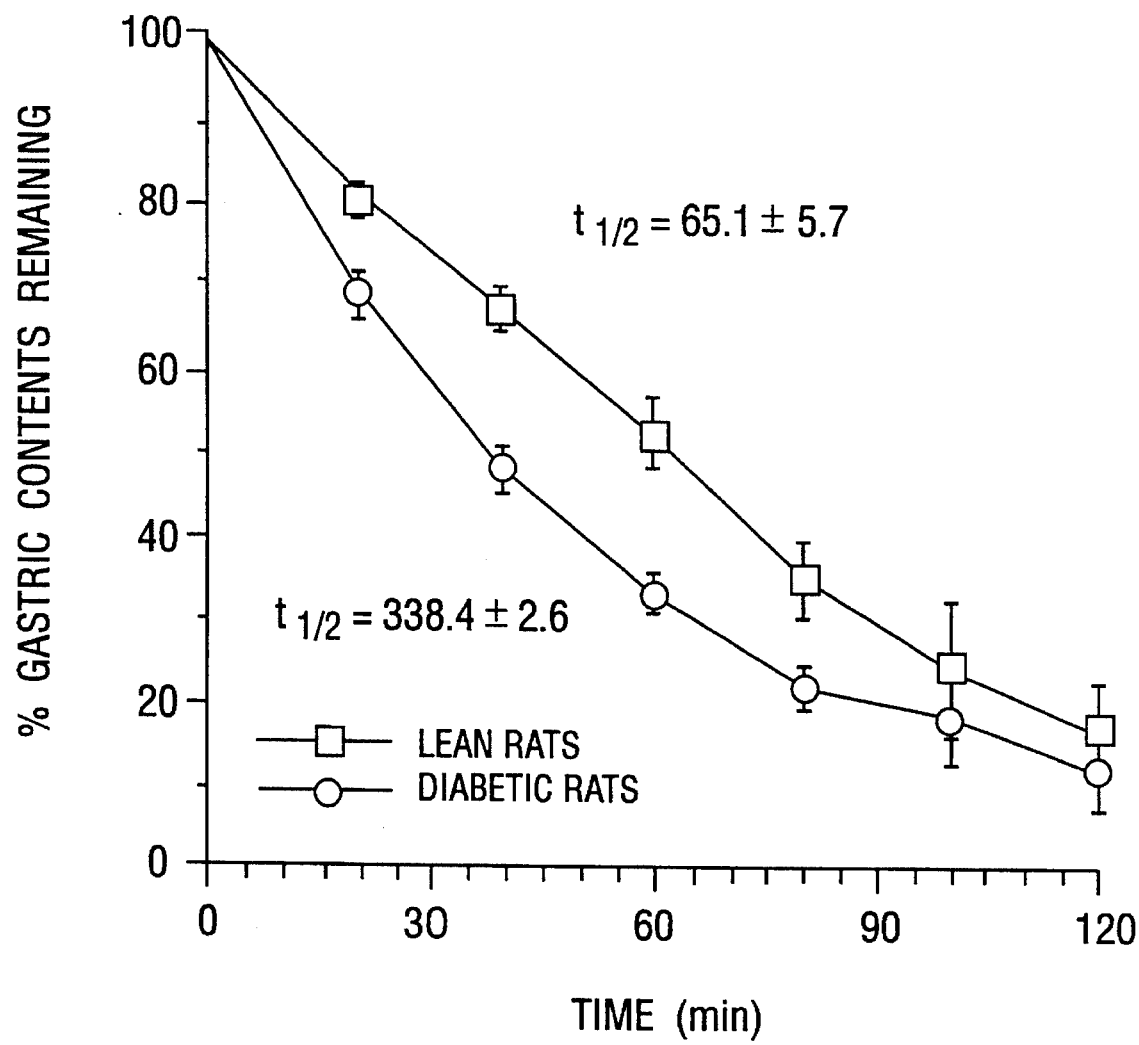
FIG. 21 shows gastric emptying rates in 10-week old diabetic and lean Zucker rats.

Gastric emptying of glucose was significantly accelerated in diabetic rats, with half-emptying times of 38.4±18 min compared to 65.1±5.7 min in lean nondiabetic rats. Results are illustrated in FIG. 21. Orally administered Camostat, a trypsin inhibitor (Ono Pharmaceuticals, Osaka, Japan) markedly slowed gastric emptying in both diabetic and lean rats, producing half-emptying times of 141±33 and 167±25 min for diabetic and lean groups, respectively. In diabetic rats without Camostat, incremental increases in plasma glucose of 270-±18 mg/dl were significantly reduced to 160±15 mg/dl by camostat.

Figure 22:
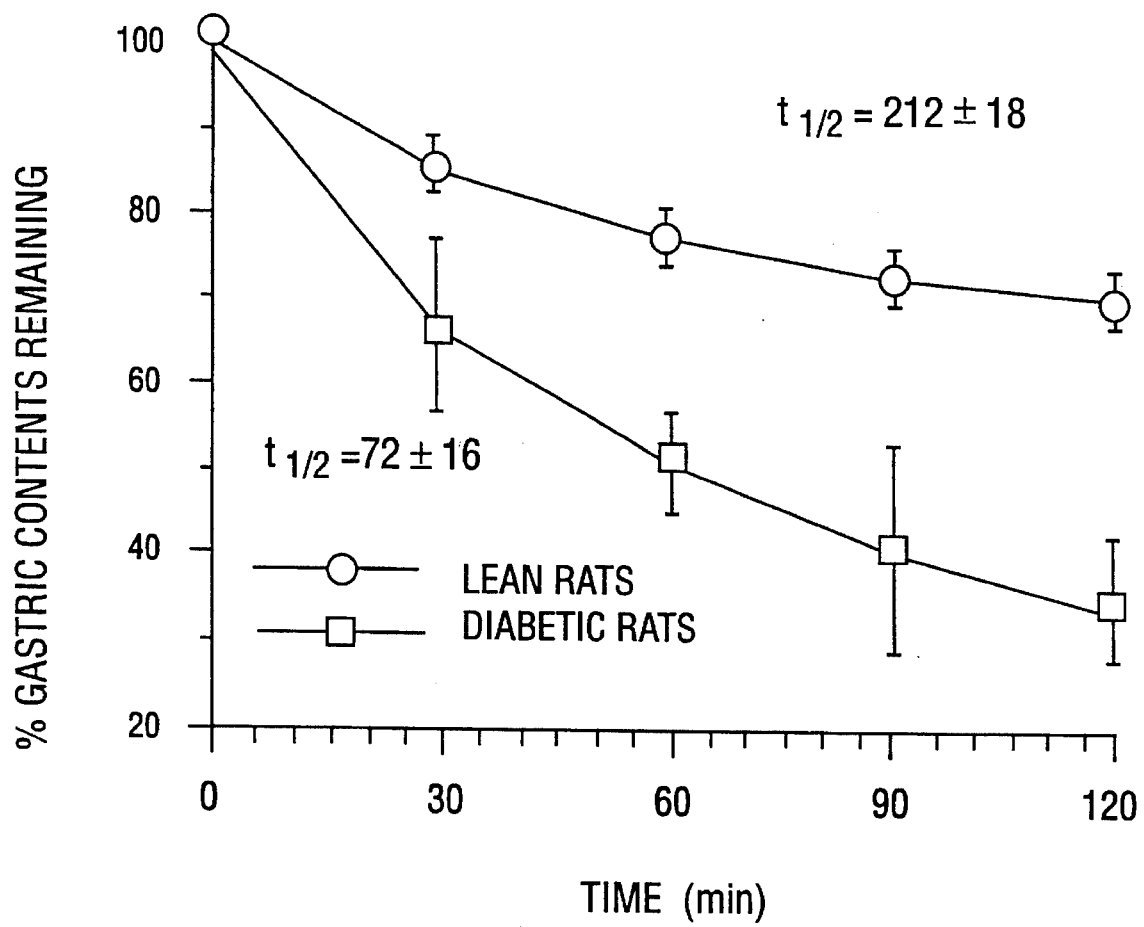
FIG. 22 shows gastric emptying rates in 18-week old diabetic and lean Zucker rats.

The persistence of abnormal gastric emptying with age was tested by checking gastric emptying in the 8 diabetic and 8 lean Zucker rats at 18 weeks of age. At this point the diabetic rats no longer were gaining weight and weighed approximately the same as the lean rats. Results showed that gastric emptying of the 30% glucose solution was slower in both groups at 18 weeks compared to 10 weeks, but the differences between lean and diabetic groups were even greater at 18 weeks than at 10 weeks. See FIG. 22 in comparison with FIG. 21.

Figure 23:
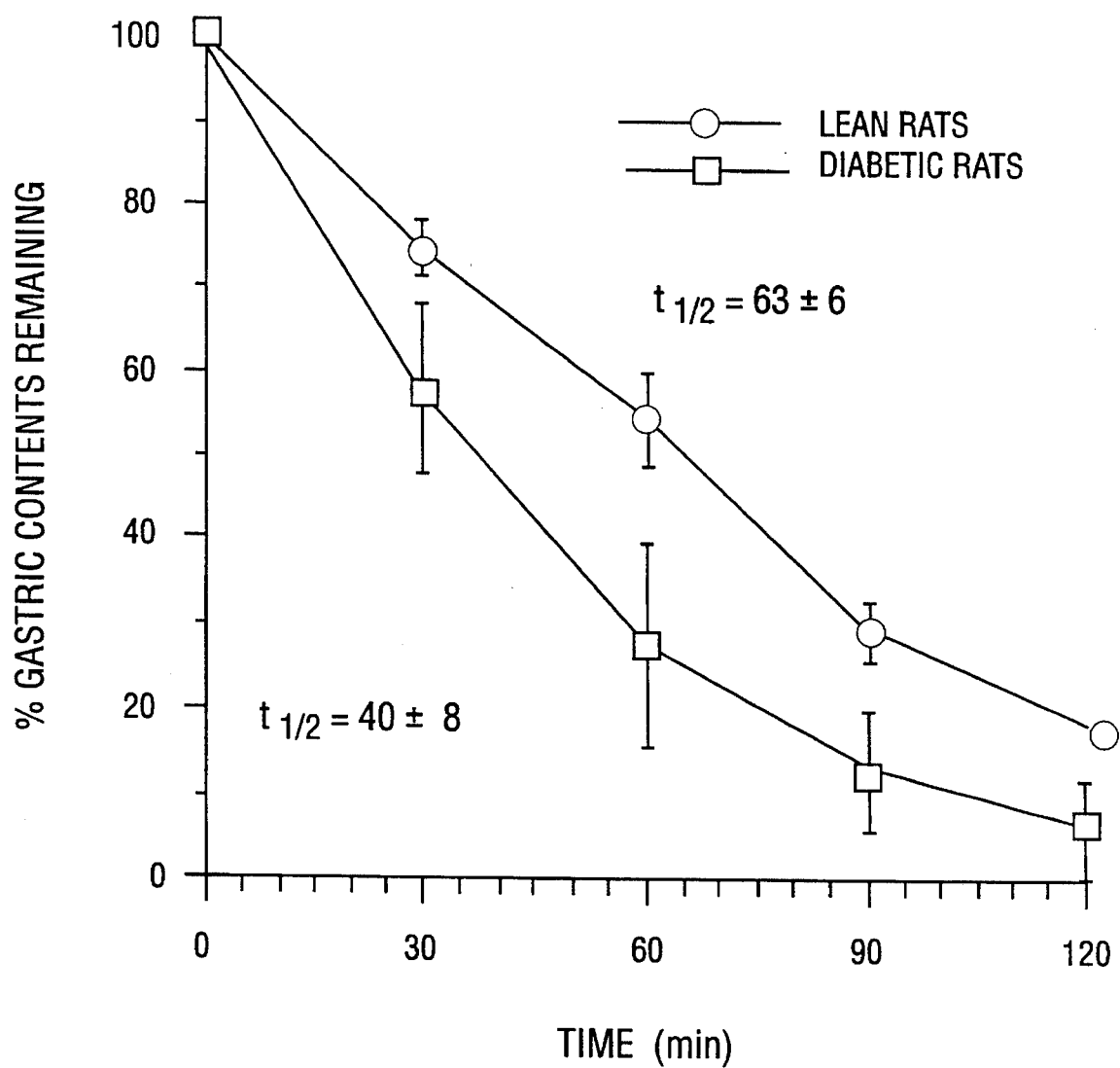
FIG. 23 shown rates of gastric emptying of a mixed meal in diabetic compared with diabetic rats.

The accelerated gastric emptying in diabetic rats compared to nondiabetic rats occurred with both pure glucose solutions and with mixed meals. This was shown in tests with 4 Zucker lean and 4 Zucker diabetic rats given a mixed, liquified meal containing by dry weight 21% soy protein, 61% carbohydrate and 6% fat. Rats were fed an amount of diet isocaloric with 30% glucose and stomach emptying followed for 120 min. Gastric half emptying times were 63±6 min in the lean rats versus 40±8 min in the diabetic rats. Results are shown in FIG. 23.

These data show that the previously described accelerated gastric emptying of glucose in human early Type 2 diabetes is reproduced in a rat model of non-insulin-dependent diabetes mellitus (NIDDM). Enhanced plasma CCK release by an oral trypsin inhibitor slows gastric emptying and attenuates increases in postprandial plasma glucose in this model.

The present invention has been described in terms of particular embodiments found by the inventors to comprise preferred modes of practice of the invention. It will be appreciated by those of skill in the art that in light of the present disclosure numerous modifications and changes can be made without departing from the intended scope of the invention. For example, other methods than drugs might be used to delay gastric emptying, such as cellulose derivatives and gastric bubbles. In addition, foods containing agents that delay gastric emptying such as trypsin inhibitors could be made and specifically targeted for consumption by diabetics. All such modifications are intended to be within the scope, spirit and concept of the invention as defined by the appended claims.

REFERENCES

The references listed below are incorporated herein by reference to the extent they supplement, explain, provide a background for or teach methodology, techniques and/or compositions employed herein.

Akkermans, L. M. A., Houghton, L. A. and Brown, N. J., Scand. J. Gastroenterol Suppl. 24, 27–31 (1989).

Brener, W., Hendrix, T. R., McHugh, P. R., Gastroenterology 85, 76–82 (1983).

Campbell, I. W., Heading, R. C., Tothill, P., :Buist, T. A. S., Ewing, D. J., Clarke, B. F., Gut 18, 462–467 (1977).

Chaudhuri, T. K and Fink, S., Am J. Gastroenterology 85, 223–231 (1990).

Christian, P. E., Datz, F. L., Sorenson, J. A., Taylor, A. Technical Factors in gastric emptying studies [teaching editorial]. *J. Nuclear Med.* 24, 264–268 (1983).

Guan, D., Green, G. M., Schwartz, J. G. and Phillips, W. T., Abstract, American Gastroenterological Assoc., Boston, Mass., May 16–19 (1993).

Hill, A. J., Peikin, S. R., Ryan, C. A. and Blundell, J. E., *Physiology and Behavior* 48, 241–246 (1990).

Horowitz, M., Harding, P. E., Maddox, A. F. et al., Diabetologia 32, 151–159 (1989).

Jenkins, D. J. A., Thomas, M. S., Wolever, M. S., Ocana, A. M., Vuksan, V., Cunnane, S. C., Jenkins, M., Wong, G. S., Singer, W., Bloom, S. R., Blendis, L. M. and Josse, R. G., Diabetes 39, 775–780 (1990).

Keshavarzian, A., Iber, F. L., Vaeth, J., Am. J. Gastroenterology 82, 29–35 (1987).

Kiyasaka, K., Nakamura, R. and Kitani, K., J. Gerontol. 44, M136–140 (1989).

Kuzio, M. Dryburgh, J. R., Malloy, K. M. and Brown, J. C.: Radioimmunoassay for gastric inhibitory polypeptide. *Gastroenterology* 66: 357–364 (1974).

Liddie, R. A., Fed. Res. in progress, *Natl. Inst. Diabetes and Dig, Dis.*, 1990

Liddie, R. A. et al., *J. Clin. Invest.* 77, 992 (1986).

Liddie, R. A., Rushakoff, R. J., Morita, E. T., Beccaria, L., Carter, J. D. and Goldfine, I. D., J. Clin Invest. 81. 1675–1681 (1988).

O'Sullivan, J. B. The interaction between pregnancy, diabetes and long-term maternal outcome in Reece, E. A. and Coustan, D. R., eds. Diabetes mellitus in pregnancy. New York: Churchill Livingstone, 1988.

Pellegrini, C. A., Broderick, W. C., VanDyke, D. and Way, L. W., Am. J. Surg. 145, 143–151 (1983).

Pettitt, D. J., Bennett, P. H., Knowles, W. C., et al., Gestational diabetes mellitus and impaired glucose tolerance in the offspring. *Diabetes* 34, 119 (1985).

Phillips, W. T., Schwartz, J. G. and McMahan, C. A. *J. Nucl. Med.* 33:1496–1500 (1992).

Phillips, W. T., Schwartz, J. G. and McMahan, C. A., *Dig. Dis. and Sci.* 37, 1992.

Schwartz, J. G., Phillips, W. T. and Aghebat-Khairy, B. Clin. Chem. 36, 125 (1990).

Smout, J. J. P. M., Z. Gastroenterol. 24/supp 2, 45–54 (1986).

Thompson, D. G., Wingate, D. L., Thomas, M. and Harrison, D., Gastroenterology 82, 51–55 (1982).

What is claimed is:

1. A method of maintaining the following glucose metabolic indicators at or near normal levels; blood glucose, C-peptide and insulin levels at fasting and during oral glucose tolerance tests, hemoglobin A1C, insulin sensitivity and GIP levels in a human having a early non-insulin dependent diabetic condition and exhibiting rapid grastric emptying, comprising administering to said individual a therapeutically effective dose of POT II, cholecystokinin, cholestyramine or camostat to effectively raise plasma cholecystokinin levels to about 2–3 fold of basal fasting levels of cholecystokinin in said human.

2. The method of claim 1 wherein the early diabetic condition is an impaired glucose tolerance, hyperinsulinemia or insulin resistance.

3. The method of claim 1 wherein the early diabetic condition is borderline diabetes, characterized by at least one of glycosuria, increased thirst, abnormally high blood glucose or insulin, insulin resistance and increased susceptibility to infection.

4. The method of claim 1 wherein the early diabetic condition is non-insulin dependent diabetes mellitus.

5. The method of claim 1 wherein the administered compound comprises POT II and a protein obtained from milk or egg white.

6. The method of claim 5 wherein the POT II effective therapeutic dose is between about 15 to about 25 mg/kg.

7. The method of claim 1 where the administration is oral or by intravenous administration.

8. The method of claim 1 wherein camostat has the structure:

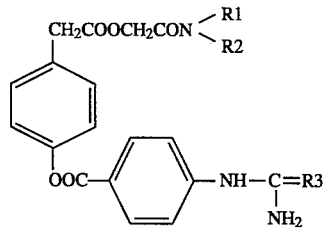

and wherein $R_1$ and $R_2$ are independently H or lower alkyl and $R_3$ is O or NH.

9. The method of claim 8 wherein the lower alkyl is methyl, ethyl, or propyl.

10. The method of claim 8 wherein $R_1$ and $R_2$ are H and $R_3$ is O.

* * * * *